US010948502B2

(12) United States Patent
Stubiger et al.

(10) Patent No.: US 10,948,502 B2
(45) Date of Patent: Mar. 16, 2021

(54) OXIDIZED LIPID DETECTION

(71) Applicant: KRATOS ANALYTICAL LIMITED, Manchester (GB)

(72) Inventors: Gerald Stubiger, Vienna (AT); Omar Belgacem, Salford (GB)

(73) Assignee: KRATOS ANALYTICAL LIMITED, Manchester (GB)

( * ) Notice: Subject to any disclaimer, the term of this patent is extended or adjusted under 35 U.S.C. 154(b) by 11 days.

(21) Appl. No.: 15/116,840

(22) PCT Filed: Feb. 9, 2015

(86) PCT No.: PCT/GB2015/050348
§ 371 (c)(1),
(2) Date: Aug. 5, 2016

(87) PCT Pub. No.: WO2015/121627
PCT Pub. Date: Aug. 20, 2015

(65) Prior Publication Data
US 2016/0349277 A1    Dec. 1, 2016

(30) Foreign Application Priority Data
Feb. 12, 2014  (GB) .................................. 1402456.6

(51) Int. Cl.
*G01N 33/92*     (2006.01)
*G01N 1/40*      (2006.01)
(Continued)

(52) U.S. Cl.
CPC ............. *G01N 33/92* (2013.01); *B03C 1/005* (2013.01); *C11B 3/02* (2013.01); *G01N 1/4044* (2013.01); *G01N 33/587* (2013.01)

(58) Field of Classification Search
CPC ........ G01N 33/92; G01N 1/40; G01N 1/4044; G01N 33/587; B03C 1/005
See application file for complete search history.

(56) References Cited

U.S. PATENT DOCUMENTS

| 2008/0311597 | A1* | 12/2008 | Castro | G01N 33/564 |
| | | | | 435/7.36 |
| 2010/0291547 | A1* | 11/2010 | Chen | C07D 311/82 |
| | | | | 435/5 |
| 2013/0122100 | A1* | 5/2013 | Lanza | A61K 9/0019 |
| | | | | 424/491 |

FOREIGN PATENT DOCUMENTS

| EP | 0 631 138 A1 | 12/1994 |
| WO | 02/086168 A1 | 10/2002 |

(Continued)

OTHER PUBLICATIONS

SciFinder record of CAS Registry No. 59177-46-7 , "Benzamide, 4-mercapto." Accessed on Jun. 11, 2018. (Year: 2018).*

(Continued)

*Primary Examiner* — Christopher Adam Hixson
*Assistant Examiner* — Michelle Adams
(74) *Attorney, Agent, or Firm* — Sughrue Mion, PLLC

(57) ABSTRACT

The present invention is concerned with a method of extracting oxidized lipids from a lipid solution, the method comprising (a) a derivatisation step, comprising contacting a derivatisation agent with the lipid solution such that aldehydic oxidized lipids and/or α,β-unsaturated oxidised lipids, if present in the lipid solution, are derivatised to include an anionic group, and (b) an oxidised lipid capture step, in which nanoparticles are contacted with the lipid solution, wherein the nanoparticles capture anionic-group containing oxidised lipids. The invention also includes a method of extracting aldehydic oxidized phospholipids from a lipid solution, the method comprising (a) a derivatisation step, comprising introduction of a anionic group to aldehydic oxidized lipids and/or α,β-unsaturated oxidised lipids in the lipid solution, and (b) an oxidised lipid capture step, in which nanoparticles are contacted with the lipid solution, (Continued)

wherein the nanoparticles bind anionic-group containing oxidised lipids.

14 Claims, 24 Drawing Sheets

(51) Int. Cl.
*C11B 3/02* (2006.01)
*G01N 33/58* (2006.01)
*B03C 1/005* (2006.01)

(56) References Cited

FOREIGN PATENT DOCUMENTS

| WO | 03/089921 A1 | 10/2003 |
|---|---|---|
| WO | 2012/152943 A1 | 11/2012 |
| WO | 2013/152325 A1 | 10/2013 |
| WO | 2014/018643 A1 | 1/2014 |

OTHER PUBLICATIONS

Yu, M.K. et al. "Targeting Strategies for Multifunctional Nanoparticles in Cancer Imaging and Therapy," Theranostics. 2012; 2(1): 3-44. (Year: 2012).*

Tsuji, Akio "Microdetection of aldehydes by ion-exchange resins," Nippon Kagaku Zasshi, vol. 84, Issue: 11, pp. 919-922 1963; including Scifinder abstract and software translation. (Year: 1963).*

Dow Water Solutions. Dowex™ Fine Mesh Spherical Ion Exchange Resins for Fine Chemical and Pharmaceutical Column Separations. Downloaded from <http://msdssearch.dow.com/PublishedLiteratureDOWCOM/dh_006f/0901b8038006f232.pdf> on Mar. 4, 2019 (Year: 2019).*

Abdelmoez, W. et al. "Production of Amino and Organic Acids from Protein Using Sub-Critical Water Technology," International Journal of Chemical Reactor Engineering, 2013; 11(1): 1-16 (Year: 2013).*

Gerald Stugiber et al., "Analysis of Oxidized Phospholipids by MALDI Mass Spectrometry Using 6-Aza-2-thiothymine Together with Matrix Additives and Disposable Target Surfaces", Anal. Chem., Jul. 1, 2010, pp. 5502-5510, vol. 82, No. 13, XP-002711505.

Yan Li et al., "Novel $Fe_3O_4@TiO_2$ Core-Shell Microspheres for Selective Enrichment of Phosphopeptides in Phosphoproteome Analysis", Journal of Proteome Research, Jun. 1, 2008, pp. 2526-2538, vol. 7, No. 6, XP055187900.

Gerald Stubiger et al. "Nanoparticle-Based Detection of Oxidized Phospholipids by MALDI Mass Spectrometry: Nano-MALDI Approach", Analytical Chemistry, Jul. 1, 2014, pp. 6401-6409, vol. 86, No. 13, XP055187441.

Beate Fuchs et al., "An update of MALDI-TOF mass spectrometry in lipid research", Progress in Lipid Research, Oct. 1, 2010, pp. 450-475, vol. 49, No. , XP027265510.

Ajoy Saha et al., "Development and assessment of green synthesis of hydrazides", Indian Journal of Chemistry, Apr. 2010, pp. 526-531, vol. 49B.

Kristin Teuber et al., "2,4-Dinitrophenylhydrazine as a New Reactive Matrix to Analyze Oxidized Phospholipids by MALDI-TOF Mass Spectrometry", Analytical Letters, 2012, pp. 968-976, vol. 45.

Helmut Hinterwirth et al., "Gold Nanoparticle-Conjugated Anti-Oxidized Low-Density Lipoprotein Antibodies for Targeted Lipidomics of Oxidative Stress Biomarkers", Analytical Chemistry, 2013, pp. 8376-8384, vol. 85.

International Search Report for PCT/GB2015/050348 dated May 15, 2015.

Written Opinion for PCT/GB2015/050348 dated May 15, 2015.

Office Action dated Oct. 30, 2019 in British Application No. GB1402456.6.

Wilbur et al., "Preparation and in vivo evaluation of radioiodinated c/oso-decaborate(2-) derivatives to identify structural components that provide low retention in tissues", Nuclear Medicine and Biology, vol. 37, No. 2, pp. 167-178, 2010 (12 pages total).

* cited by examiner

OXIDIZED LIPID DETECTION

CROSS REFERENCE TO RELATED APPLICATIONS

This application is a National Stage of International Application No. PCT/GB2015/050348 filed Feb. 9, 2015, claiming priority based on British Patent Application No. 1402456.6 filed Feb. 12, 2014, the contents of all of which are incorporated herein by reference in their entirety.

FIELD

The invention relates to methods for detection of oxidized lipids.

BACKGROUND

Oxidized biomolecules are known to deteriorate the quality and increase the toxicity of food, pharmaceuticals and other industrial products. They are also known to contribute to some pathological processes, including for example, atherosclerosis, neurodegenerative disease, multiple sclerosis, diabetes and cancer. Oxidised phospholipids (OxPLs) and oxidised cholesterol esters (OxCEs) are known to play a role in oxidative stress, chronic inflammation and the formation of oxidized low-density lipoprotein (OxLDL) in vivo[1][2][3], which plays a crucial role in the onset and progression of atherosclerosis. OxPLs and OxCEs are essential components of modified human LDL[4] and HDL respectively[5].

Polyunsaturated fatty acid residues [for example, arachidonate (20:4) or linoleate (18:2)] in lipid molecules are typically the targets of reactive oxygen species in biological systems. Natural phospholipids typically comprise a phosphate-containing polar head group and two fatty acid residues esterified to a glycerol backbone. Natural cholesterol esters (CEs) comprise a neutral cholesteryl backbone and one esterified FA residue. Each can be oxidized by radical catalysed enzymatic and/or chemical mechanisms.

Consequently, due to the importance of lipid oxidation in biological processes "oxidative lipidomics" is now becoming an emerging field of interest. The development of novel assays allowing the sensitive detection, localization and quantification of the individual molecular species present in biological samples (e.g. plasma, tissues, etc.)[6] is key to this emerging field.

Soft ionisation mass spectrometry techniques are commonly used in biomolecule analysis. MALDI-MS has been used to analyse oxidized lipids extracted from biological samples[7], with speed of analysis, instrument robustness and excellent sensitivity all aiding in this analysis.

However, detection and quantification of oxidised lipids from crude biological samples (e.g. human plasma) is often compromised by (a) their low abundance in vivo, (b) the interference of more abundant isobaric compounds (e.g. non-oxidized lipids), (c) the lack of chromatographic selectivity, and (d) ionisation suppression during mass spec analysis.

To improve the detection of oxidised phospholipids from biological samples, fluorescence labelling combined with reversed-phase high-performance liquid chromatography (RPHPLC) separation has been used[5][9]. The structural characterisation of OxPLs has been improved by microderivatisation techniques using specific reagents as mass-tags, followed by RPHPLC and subsequent analysis by ESI-MS[10][11][12]. Further, other derivatisation strategies have been developed to improve the detection and extend the mass of lipid oxidisation products accessible for analysis by ESI[13] and MALDI-MS[14].

Numerous techniques have been proposed for the separation and enrichment of OxPLs from bulk lipids in biological samples (e.g. human plasma) followed by MALDI-MS analysis[7]. Such methods can be used for the screening of OxPLs from clinical samples[15]. However, the methods are typically complex, which can prevent their implementation in routine clinical applications.

The inventors recently disclosed a simple, robust and reproducible method for the extraction of OxPLs. The method uses metal oxide ($MeO_2$) nanoparticles (e.g. $SnO_2$, $TiO_2$, and $ZrO_2$) which were found to selectively bind carboxy group containing OxPCs) over other OxPL and PL species. Subsequent analysis of the OxPLs by MALDI-MS is then possible.

The high surface-to-volume ratio of nanoparticles allows extremely efficient extraction and concentration of oxidized phospholipids (OxPLs). The problems of direct analysis from crude biological samples (low abundance, and interference of other isobaric compounds) are no longer relevant.

However, since the $MeO_2$ nanoparticles selectively bind to carboxy groups, the disclosed method can only be used to extract and analyse OxPLs which contain a carboxy group.

SUMMARY OF THE INVENTION

At its most general, a first aspect of the invention provides a method of extracting oxidised lipids, suitably oxidised phospholipids (OxPLs) using nanoparticles, wherein α,β-unsaturated, aldehydic and carboxylic terminated oxidised lipids (suitably OxPLs) can be extracted.

Short-chain oxidised lipids containing truncated Ω-terminal aldehydic or carboxylic sn-2 fatty acid residues (e.g. POVPC or PGPC) are known to be particularly relevant in biological processes[16]. These oxidised lipids have a biphasic action, with cell proliferative effects at low concentrations and apoptotic effects at higher concentrations. Further, aldehydic and carboxylic oxidised lipids have been shown to have different effects on cell proliferation[17][18].

α,β-unsaturated oxidised lipids (e.g. KDdiA-PC) are another significant, biologically important oxidative stress biomarker molecules that can be detected according to the methods of the invention.

The simple, reliable method according to the first aspect of the invention, allows α,β-unsaturated, aldehydic and carboxylic terminated oxidised lipids (suitably OxPLs) to be extracted (and optionally, subsequent analysed). This increases the information content of the extracted oxidised lipid (suitably OxPL) sample. The method also benefits from using a nanoparticle-based extraction technique. For example, nanoparticles are simple to use, and have a high surface area to volume ratio, allowing efficient extraction.

Specifically, the invention provides a method of extracting oxidized lipids (suitably OxPLs) from a lipid solution, the method comprising
 (a) a derivatisation step, comprising contacting a derivatisation agent with the lipid solution such that aldehydic oxidized lipids and/or α,β-unsaturated oxidised lipids (suitably OxPLs), if present in the lipid solution, are derivatised to include an anionic-group, and
 (b) an oxidised phospholipid capture step, in which nanoparticles are contacted with the lipid solution, wherein the nanoparticles capture anionic-group containing oxidised lipids (suitably OxPLs).

Throughout this specification, reference to an anionic group may preferably refer to a carboxy group (i.e. $RCOO^-$), a nitrate ($RNO_3^-$) or to a sulphate group (i.e. $RSO_3^-$). In more preferred cases, reference to an anionic group refers to a carboxy group or a sulphate group, with carboxy being most preferred because this is the most common anionic group in oxidised lipids in vivo. Nevertheless, other anionic groups could be used.

Throughout this specification, reference to oxidised lipids may preferably refer to oxidised phospholipids (OxPLs), and/or oxidised cholesterol esters (OxCEs). In more preferred cases, it refers to oxidised phospholipids (OxPLs).

The invention also provides a method of extracting aldehydic oxidized lipids (suitably OxPLs) and/or α,β-unsaturated oxidised lipids (suitably OxPLs) from a lipid solution, the method comprising
(a) a derivatisation step, comprising introduction of an anionic (suitably carboxy) group to aldehydic oxidized lipids and/or α,β-unsaturated oxidised lipids (suitably OxPLs) in the lipid solution, and
(b) an oxidised lipid (suitably OxPL) capture step, in which nanoparticles are contacted with the lipid solution, wherein the nanoparticles capture anionic-group (suitably carboxy-group) containing oxidised lipids (suitably OxPLs).

As used herein, the term "capture" incorporates any form of binding between the nanoparticles and the captured lipids. This is preferably physical binding. The binding may rely on ionic or static interactions. In preferred cases, the binding relies on electrostatic interactions. It may be an electrophilic-nucleophilic interaction.

The oxidised lipid (suitably OxPLs) capture step (b) (in any aspect of the invention) may preferably be an oxidised lipid enrichment step, in which nanoparticles are contacted with the lipid solution, wherein the nanoparticles selectively bind anionic-group (suitably carboxy-group) containing oxidised lipids (suitably OxPLs) over other lipid types.

As used herein, the term "selectively bind" indicates that oxidised lipids (suitably OxPLs) are bound to the nanoparticles in preference to other groups, particularly in preference to other lipids, and even more particularly, in preference to unoxidised lipids. In preferred cases, the nanoparticles preferentially bind the anionic (suitably carboxy) group all other groups, and in particular over the phospho group of oxidised phospholipids (where present) and/or over the cholerteryl group of OxCEs (where present). That is, they preferentially bind directly to the anionic-group (e.g. carboxy-group) of anionic-group containing OxPLs or OxCEs over other groups in oxidised biomolecules/lipids.

In other words, the selective binding nature of the nanoparticles can mean that the proportion of oxidised lipids (suitably OxPLs) in the bound molecules is greater than the proportion of oxidised lipids (suitably OxPLs) in the lipid solution. For example, the proportion of oxidised lipids (suitably OxPLs) in the bound molecules may be at least 3, 5, 10, 15 or 20, 50 or 100 or more times the proportion of oxidised lipids (suitably OxPLs) in the lipid solution.

In some cases, the selective binding nature of the nanoparticles means that at least 40 wt %, 50 wt %, 60 wt %, 70 wt %, 80 wt % or 90 wt % of the bound molecules are oxidised lipids (suitably OxPLs). In some cases, the nanoparticles will substantially only bind oxidised lipids (suitably OxPLs) (i.e. >85 wt %, >90 wt %, >95 wt % or 100 wt % of bound molecules are oxidised lipids (suitably OxPLs)).

Note that unoxidized phospholipids containing anionic groups commonly exist in vivo (such as phosphtidylserine-glycerol, or phosphoinositides) but these do not effectively bind to nanoparticles and are are usually present in very low concentrations (e.g in human and mouse plasma). Thus, their nanoparticle-bound concentration is relatively very low, and they have little effect on the oxidised lipid capture/enrichment. Further, they can be easily detected in further analysis of the bound species and differentiated from the oxidised lipid signals (e.g. OxPCs are exclusively detected in positive mode while anionic phospholipids will only be detected in the negative mode).

For example, subsequent analysis by MALDIMS/MS allows these unoxidised phospholipids to be identified by their different fragmentation characteristics. (This is a further reason why the use of MALDI-MS/MS in subsequent analysis is preferred (see below).

The term "nanoparticles" as used herein relates to particles ranging in diameter from about 0.01 nm, 0.1 nm, 0.5 nm, 1 nm, 3 nm or 5 nm to about 10000 nm, 8000 nm, 5000 nm, 2000 nm, 1000 nm, 999 nm, 800 nm, 500 nm, 200 nm, 100 nm or 50 nm.

In preferred cases, at least about 0.05 µg/L, 0.1 µg/L, 0.15 µg/L, 0.2 µg/L or 0.4 µg/L of nanoparticles are added to the sample solution. These are generally sufficient to detect physiological concentrations of oxidised lipids in normal and diseased conditions.

In preferred cases, less than about 2 µg/L, 1.5 µg/L or 1 µg/L are added. A greater concentration can affect MALDI analysis of the sample.

The nanoparticles used in the first aspect of the invention are not particularly limited, provided that they preferentially bind anionicgroup (suitably carboxy-group) containing oxidised lipids over other (non-anionic-containing) oxidised lipids and other non-oxidised lipids. In preferred cases, they preferentially bind anionic (suitably carboxy) groups over phospho or cholesteryl groups.

In the methods of the first aspect, the nanoparticles may comprise one or more metal oxides ($MeO_2$), or may consist of one or more metal oxides. In some cases, the metal oxide ($MeO_2$) is selected from tin oxide, zirconium oxide and titanium oxide nanoparticles. Nanoparticles comprising zirconium oxide ($ZrO_2$) are favoured because they are widely compatible with MALDI matrix materials, and show a very high degree of selectivity for oxidised lipids (suitably OxPLs).

At its most general, a second aspect of the invention provides an alternative extraction method for oxidised lipids (suitably OxPLs) using nanoparticles. The second aspect of the invention uses different nanoparticles to those used in the method previously disclosed by the inventors.

Specifically, the invention provides a method of extracting oxidized lipids (suitably OxPLs) from a lipid solution, the method comprising
(b) an oxidised lipid (suitably OxPL) capture step, in which nanoparticles are contacted with the lipid solution, wherein the nanoparticles capture anionic-group (suitably carboxy-group) containing oxidised lipids (suitably OxPLs),
wherein the nanoparticles comprise a magnetic core, and wherein the core is surface functionalised such that the surface is electrophilic.

As discussed above, the oxidised lipid (suitably OxPL) capture step may be an oxidised lipid enrichment step.

The method of the second aspect may further comprise prior to step (b),
(a) a derivatisation step, comprising contacting an anionic-group (suitably carboxy-group) containing derivatisation agent with the lipid solution under such conditions that aldehydic oxidized lipids (suitably OxPLs) and/or α,β-unsaturated oxidised lipids (suitably OxPLs), if present in the lipid solution, are derivatized to include said anionic-group (suitably carboxy-group).

Alternatively the method of the second aspect may further comprise prior to step (b), (a) a derivatisation step, comprising introduction of a anionic-group (suitably carboxy-group) to aldehydic oxidized lipids and/or α,β-unsaturated oxidised lipids (suitably OxPLs) in the lipid solution.

Where a step (a) is present, the method of the second aspect can then extract derivatised aldehydic oxidised lipids (suitably OxPLs) and/or derivatised and/or α,β-unsaturated oxidised lipids (suitably OxPLs) and anionic-group (suitably carxboy-group) containing oxidised lipids (suitably OxPLs), increasing the information content of the extracted sample. A wider range of oxidized lipids (suitably OxPLs) can be extracted, detected, quantified and/or identified.

The nanoparticles used in the methods of the second aspect comprise a magnetic core, wherein the core is surface functionalised such that the surface is electrophilic. The core may be surface functionalised such that the nanoparticles capture anionic-group (suitably carboxy-group) containing oxidised lipids by an anion-exchange mechanism, or alternatively by an ion-pairing mechanism.

In some cases, the core is or comprises silanized iron oxide, carbon-coated cobalt and magnetic iron oxide. In some cases, the core may comprise or consist of metallic iron oxide, or $Fe_3O_4$. In some cases, the core is surface functionalised such that the surface is hydrophilic. In some cases, the surface functionalization may bind anionic-group (suitably carboxy-group) containing oxidised phospholipids by an anion-exchange mechanism.

In some cases, the functionalised surface comprises or consists of a polymer. In some cases, the functionalised surface comprises an amine or a polyetheramine.

Amine (denoted MAG-NH2 nanoparticles) or polyetheramine (denoted MAG-PEA nanoparticles) surface functionalization is preferred because these groups are fully compatible with solvents used in other stages (for example, in dissolving the MALDI matrix material, or in the lipid extraction step, where present).

The nanoparticles described in relation to the second aspect can also be used in the method of the first aspect.

Suitably, the nanoparticles used in either the first or second aspect do not comprise or consist of gold.

The methods of both aspects defined herein selectively extract OxPLs, thereby enhancing the OxPL concentration for subsequent detection. The detectable OxPL concentration in the lipid solution is therefore much lower. For example, in some cases the lowest detectable OxPL concentration in the lipid solution is about 80 nM using MALDI-MS. In such cases, after application of the methods described herein, OxPL concentrations of about 0.2 nM are detectable.

This enhancement can be quantified by the enhancement factor, defined herein as

Enhancement factor=(detectable OxPL concentration without using nanoparticles)/(detectable OxPL concentration with nanoparticle extraction).

In the above example, the enhancement factor is about 400. In some cases, the enhancement factor is at least about 100, 200, 300, 400, 500, 750 or 1000.

The methods described above allow detection of OxPLs at sub-nanomolar concentrations. This is several (1-4) orders of magnitude more sensitive than is necessary for the detection of OxPLs usually present in vivo (e.g. in animal or human plasma).

A further aspect of the inventions pertains to a kit for implementing a method of any previous aspect. The kit comprises reagents necessary to implement the method, and a detailed protocol explaining each step in the method.

WO 2012/152943 A1 (WO'943 hereonin) describes derivatisation of carbonylated OxPLs to allow detection/analysis by MALDI-MS. In one example, gold nanoparticles are used to extract the derivatised particles. However, the method of WO'943 differs from that claimed herein in that in the derivatisation step, a thiol group is introduced (compared to an anioinic or acidic group in the claimed invention). The thiol group in the prior art chemically bonds to the nanoparticle support to allow extraction, whereas the present invention is based on electrostatic interaction of the nanoparticles with the OxPLs to be extracted.

WO'943 aimed to develop a mass-tag that specifically reacts with carbonylated biomolecules and can be used for the selective extraction of the derivatized target molecules for subsequent MS analysis. The application particularly focuses on oxidized proteins and peptides obtained by tryptic digestion of the proteins (see pages 19-20). Since peptides and proteins per se contain a number of charged groups (e.g. basic or acidic amino acids) an extraction strategy based on anionic or acidic groups (i.e. introduction of a carboxyl group) would not make sense. Thiol-chemistry is used for the interaction of the biomolecules with the gold extraction surface by formation of either disulfide bonds ("dative" binding to gold surface). To exploit this strategy, 4-sulfanylbenzohydrazide (PACA) was used as the derivatization reagent. However, the approach of WO'943 has several disadvantages associated with it, relative to the new and inventive methods described herein. These are:

1) The ionization efficiency of PACA-derivatized OxPLs (e.g. PACA-POVPC) is considerably lower than other derivatization reagents like 2-AA (as used herein). The detection limit with PACA-POVPC was 2 pmol while in the present case it is in the range of 10 fmol (~5 pg) on the MALDI target.

2) The SH-group in PACA can easily form dimers via disulfide bonding between PACA molecules leading to signal splitting between OxPLs derivatized with the PACA mono- and dimers, respectively. This complicates mass spectral analysis and reduces the sensitivity of MALDI detection. To mitigate this problem, PACA has first to be immobilized on a solid support (e.g. thio-sepharose) before reacting with the carbonyl compounds which increases the process time and reduces throughput.

3) Disulfide bonding as well as dative binding are both strong covalent bindings and thus reducing agents (e.g. DTT) in relatively high concentration (e.g. 100 mM) are needed to release the PACA-bound molecules from the surface of the chromatographic material (e.g. PACA-sepharose column, page 21) or from the gold nanoparticles. Consequently, the concentration effect of OxPLs caused by NP-binding is lost; the strong binding can lead to sample losses, reducing the overall sensitivity. Further, the need for a sample release step prevents direct MALDI-MS analysis of the NP-bound OxPLs. This extra step increases processing time and reduces throughput.

4) Gold nanoparticles are not stable in organic solvents (e.g. MeOH or Acetone) such as those used for OxPL extraction from biological samples.

5) The WO'943 method allows analysis of only derivatised ALDO-OxPLs but not other naturally occurring OxPLs (e.g. CARBO-OxPLs) because the Gold nanoparticles/thiol-containing media are not specific. This considerably limits the applicability of their method for oxidized lipid analysis in general.

The methods described and claimed herein have the following advantages over the WO'943 disclosure.

1) A ~200-fold increases in sensitivity that the WO'943 method.

2) The derivatization reagents useable with the methods described herein (e.g. 4-AA) do not form dimers and can be reacted with OxPLs directly in solution without the problem of signal splitting and the need for immobilization on the NP-surface.

3) The electrostatic interaction of anionic (e.g. carboxyl) groups with the NPs is much weaker than the covalent bonding of the thiols allowing for a direct analysis of OxPLs from the NP-surface by MALDI-MS without the need for using any releasing-agents.

Thus the concentration effect of OxPLs binding to the NP-surface is preserved resulting in a very high sensitivity, which is necessary to detect the low levels of oxidized lipids in biological samples and makes the whole procedure much easier to use.

4) The surface-functionalised NPs described herein (e.g. MAG-PEA) we use in our approach are fully compatible with the solvents necessary for extraction of OxPLs from biological samples.

5) The method described and claimed herein allows simultaneous analysis of both ALDO- and CARBO-OxPLs thus covering the whole range of the most prevalent short-chain OxPLs from biological samples.

In summary, the methods described here represent a considerable improvement for the detection of oxidized lipids (e.g. OxPLs) by MALDI-MS.

Various optional and preferred features are discussed below. Each optional and preferred feature, and combinations thereof, are explicitly disclosed herein with each and every aspect of the invention, to the extent that they are compatible, as if each and every combination was individually and explicitly recited.

Derivatisation Step

Where present, the derivatisation step introduces an anionic (suitably carboxy) group into aldehydic oxidized lipids (suitably OxPLs) (if present) in the lipid solution.

A derivatisation agent is used. Optionally, this may be used as a mass-tag, which aids in subsequent detection, identification and/or characterisation of aldehydic oxidised lipids (suitably OxPLs) and/or α,β-unsaturated oxidised lipids (suitably OxPLs). It also moves the signal to a higher m/z value, and away from the typically seen low-m/z noise.

Preferably, the derivatisation agent contains an anionic (suitably carboxy) group, which is introduced into the aldehydic oxidised lipids (suitably OxPLs) and/or α,β-unsaturated oxidised lipids (suitably OxPLs) (if either is present). That is, the derivatisation step may comprise contacting a anionic-group (suitably carboxy-group) containing derivatisation agent with the lipid solution such that aldehydic oxidized lipids (suitably OxPLs) and/or α,β-unsaturated oxidised lipids (suitably OxPLs), if present in the lipid solution, are derivatised to include said anionic-group (suitably carboxy-group).

Suitably, the derivatisation agent may also introduce an aromatic group into the oxidised lipids (suitably OxPLs). Aromatic groups are good mass-tags and are easily ionised in any subsequent MS-based analytical technique or can additionally be used for spectrophotometric (e.g. fluorescence) detection. This helps the selective detection of the derivatised molecules during chromatographic separation using e.g. high-performance liquid (HPLC) or thin-layer (TLC) chromatography respectively.

The derivatisation agent may be a single compound or a mixture of compounds. For example, it may comprise a derivatisation reagent and a reducing agent.

In some cases, the derivatisation step comprises a reductive amination. In such cases, the derivatisation agent comprises at least an amino group and an anionic group (e.g. a carboxy group). It may additionally comprise an aromatic ring (which aids ionisation in MALDI analysis). For example, the derivatisation agent may comprise or be selected from 2-aminoantranilic acid (2AA), 4-aminoantranilic acid (4AA), 3-(4-aminophenyl)-propionic acid (4APA) and 6-aminocaproic acid (GACA). The carboxy group of these compounds is introduced to aldehydic oxidised lipids (suitably OxPLs). The aromatic group in 2AA, 4AA and 4APA is also introduced into aldehydic oxidised lipids. A derivatisation agent that is or comprises 4AA is particularly favoured, because this reacts easily, is easily ionized and binds well to nanoparticles post derivatisation.

The derivatisation agent for reductive amination may additionally comprise a reducing agent, such a sodium cyanoborohydride.

In some alternative cases, the derivatisation step comprises a hydrazone formation. In such cases, the derivatisation agent comprises a compound having a hydrazide group and an anionic (suitably carboxy) group. It may additionally have an aromatic or heteroaromatic group (which aids in ionisation during subsequent MALDI analysis).

A derivatisation step that comprises a hydrazone formation is particularly preferred because it does not need the addition of a reducing agent (e.g. sodium cyoanoborohydride) for the reaction. Such derivatisation agents react with aldehydic oxidised lipids (suitably OxPLs) to introduce an anionic (suitably carboxy) group which will bind to the surface of the nanoparticles. Additionally, these derivatisation agents also react with α,β-unsaturated oxidised lipids (suitably OxPLs e.g. KDdiA-PC) to introduce an anionic (suitably carboxy) group. Thus, where the derivatisation step comprises a hydrazine formation, this group of biologically important oxidative stress biomarker molecules can be detected.

In other words, in such cases, the derivatisation step (a) may comprise contacting an anionic-group (suitably carboxy-group) containing derivatisation agent with the lipid solution under such conditions that aldehydic oxidized lipids (suitably OxPLs) and/or α,β-unsaturated oxidised lipids (suitably OxPLs), if present in the lipid solution, are derivatized to include said anionic-group (suitably carboxy-group).

Alternatively, in such cases the derivatisation step (a) may comprise comprising introduction of a anionic-group (suitably carboxy-group) to aldehydic oxidized lipids (suitably OxPLs) and/or α,β-unsaturated oxidised lipids (suitably OxPLs), present in the lipid solution.

The inventors have found that compounds of the formula (I) are particularly suitable for use as a derivitising agent in a hydrazone formation reaction;

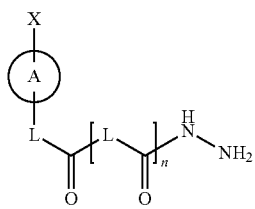

(I)

or a salt, solvate or hydrate thereof;

wherein

X represents an anionic group or an acidic group;

each L independently represents a single bond or linker group;

n is an integer from 0 to 4; and

A represents an optionally substituted heteroaryl or aryl group.

Where X is an anionic group, the compound includes a counter ion, such as primary, secondary, tertiary or quaternary ammonium ions, Na⁺, K⁺ and the like.

Where X is an acidic group, it may be a carboxylic, nitric or sulphuric acid group. Carboxylic and sulphuric acid groups are preferred, with carboxylic acid being most preferred.

In some cases, each L may independently be an alkylene, preferably a $C_{1-6}$ alkylene linker. This may be interrupted by one or more heteroatoms selected from O, S and N. In one case, it may terminate in a nitrogen atom, such that it forms a peptide linkage with the adjacent carbonyl group. In preferred cases, L represents a single bond.

n may be an integer from 0 to 4. n may be 1. n may be 2. n may be 3. n may be 4. n is preferably 0.

Group A may be an optionally substituted heteroaryl or aryl group. In some cases, A may be a monocyclic or polycyclic group. In some cases, group A may be furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl, and is optionally substituted with one or more substituents —$R_S$.

Unsubstituted phenyl is the most preferred A group.

Each $R_S$ is independently alkyl, alkenyl, alkynyl, ether, amine, halo (F, Cl, Br or I), hydroxyl (OH), cyano (CN), and nitro ($NO_2$), and wherein each $R_S$ group selected from alkyl, alkenyl, alkynyl, ether and amine is optionally substituted with one or more of alkyl, alkenyl, alkynyl, ether, amine, halo, hydroxyl, cyano, and nitro, Moiety X may be ortho, meta or para on the ring A to the moiety carrying the hydrazide group (RHN—$NH_2$). It is preferably para.

The compound of formula 1 is preferably selected from the following compounds;

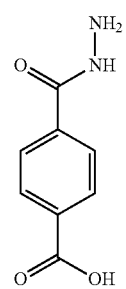 [SMILES: NNC(=O)c1ccc(C(=O)O)cc1]

(A)

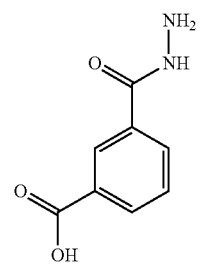

(B)

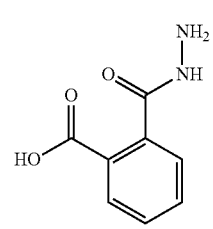

(C)

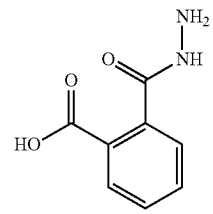

(D)

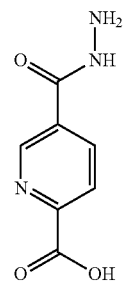

(E)

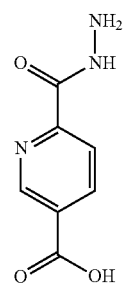

(F)

-continued

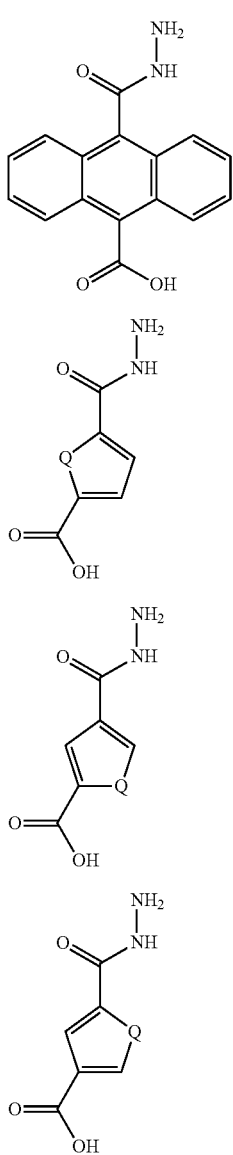

in which Q is selected from N, O and S.

The compound of formula (I) is preferably (A), that is;

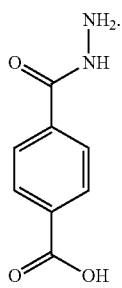

This compound is 4-carboxybenzohydrazide (4-CBH).

Such compounds can be synthesised according to the methods illustrated below for 4-carboxybenzohydrazide, 4-sulfobenzohydrazide and 4-n itrobenzohydrazide. The other compounds defined above can be synthesised by these methods, using a different starting material.

Synthesis of Benzohydrazide Derivatives with Anionic Functional Groups

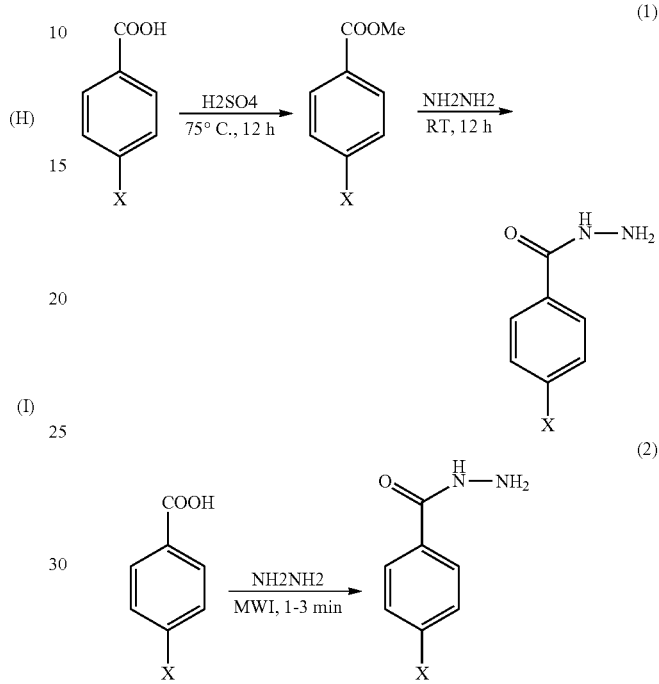

Alternative protocol using microwave irradiation (MWI) [according to A. Saha et al., Indian Journal of Chemistry, Vol 49B, pp 526-531, 2010]
Precursors:
X = COOH (terephtalic acid, TPA)
X = SO3H (4-sulfobenzoic acid)
X = NO2 (4-nitrobenzoic acid)
Products:
X = COOH (4-carboxybenzohydrazide, 4-CBH)
X = SO3H (4-sulfobenzohydrazide, 4-SBH)
X = NO2 (4-nitrobenzohydrazide, 4-NBH)

The conditions for the derivatisation step may be any such that the aldehydic and/or α,β-unsaturated oxidised lipids (suitably OxPLs) are derivatized, whilst other lipids in the solution (e.g. unoxidised PLs) are not affected.

The derivatisation agents may be used at a concentration of from about, 5 µM, 10 µM, 15 µM or 17 µM to about 23 µM, 25 µM, 30 µM or 35 µM when added to the lipid sample. They may be used at a concentration of about 20 µM. In other words, the concentration is preferably about 600-1000 times the lipid concentration, preferably about 800.

The derivatisation step preferably takes place between about 10° C., 15° C. or 20° C. to about 30° C., 35° C. or 40° C. It may take place at about 25° C. The reaction may take place over between about 5 mins, or 10 mins to about 45 mins or 60 mins. The reaction may take place over about 15 mins.

Extraction Step

In any aspect of the invention the nanoparticles may be added to the lipid solution.

In such cases, the method of any aspect may further comprise after step (b)

(ci) an extraction step, comprising extraction of the nanoparticles from the lipid solution.

The nanoparticles may be extracted from the lipid solution by centrifugation, or where the nanoparticles are magnetic, by using a magnet.

Alternatively, the nanoparticles may be fixed to a surface. For example, they may be fixed to a MALDI sample plate. In such cases, no extraction step is necessary.

Washing Step

The method of any aspect may further comprise, after step (b) and after step (ci) if present, (cii) a washing step, comprising washing the nanoparticles to remove excess lipid solution.

Preferably the nanoparticles are washed in any organic solvent, which can dissolved oxidised lipids (suitably OxPLs).

The organic solvent compositions described below as suitable for use in the lipid extraction step are suitable for use in the washing step. The compositions used in each step need not be the same. However, in preferred cases, the nanoparticles are washed in the same organic solvent composition as that used in the lipid extraction step (described below), which improves the possible rate of sample throughflow/analysis.

Lipid Extraction

In any aspect of the invention, the method may further comprise an initial step of (i) lipid extraction, comprising extraction of the lipid solution from a biological sample.

Typically, the lipid extraction step comprises addition of an organic extraction composition to the biological sample of interest (e.g. plasma, cells, tissue, microbes, etc.). The organic extraction composition preferably comprises one or more organic solvents. In some cases, the organic extraction composition preferably comprises one of more alcohols. The organic extraction composition preferably comprises more than about 50 vol % alcohol, more preferably at least about 55 vol %, 60 vol %, 70 vol %, 80 vol % or 90 vol %. Short-chain alcohols are preferred, such as $C_{1-4}$ alcohols, with ethanol and methanol particularly favoured because they have been found to effectively extract phospholipids and cholesterol esters from almost all biological samples, independent of the cellular structure. In some cases, the extraction composition comprises up to 100 vol % alcohol, preferably up to 95 vol %, 90 vol %, 85 vol %, 80 vol %, 75 vol % or 70 vol %.

Such extraction compositions can be used to wash the nanoparticles after extraction (as discussed above) and are compatible with the nanoparticles.

The organic extraction composition may alternatively or additionally comprise ketones, esters, and/or ethers (e.g. methyltertiarybutylether (MTBE), diisopropylether (DIPE)), or mixtures thereof.

These solvents are preferred because they are compatible with (i.e. they readily dissolve) the MALDI matrix materials used in the sample preparation step. For this reason, the alcohol based solvents (which comprise at least about 50 vol % alcohol) are particularly favoured. As a result of this compatibility, these solvents generate relatively small background noise signals in the resultant mass spectra. Lipid (and particularly phospholipid) extraction is efficient and reliable, allowing for reproducible spectra to be obtained. Further, no additional reagents are needed, saving cost.

Another preferable feature of the extraction composition is that it is not bi-phasic. In other words, it entirely comprises either polar solvents, or non-polar solvents. No separation step is then necessary, reducing processing time and increasing throughput. In other words, the lipid extraction step simply comprises addition of the solvent to the sample, i.e. it is a single step extraction method. This is in contrast to the Folch reagents, which require the polar and non-polar components to be phase separated after lipid extraction.

In some cases, the extraction composition does not include any halogenated organic solvent. That is, chloroform ($CHCl_3$) is specifically not part of the extraction composition. In other cases, the extraction composition comprises less than 5 vol %, preferably less than 4 vol %, 3 vol %, 2 vol %, 1 vol %, 0.5 vol %, 0.4 vol %, 0.3 vol %, 0.2 vol % or 0.1 vol % of any halogenated organic compounds or solvents (including chloroform).

In some cases, the organic extraction composition preferably comprises or consists of alcohols, as they result in the smallest spectral noise. $C_{1-4}$ alcohols are favoured, and methanol is particularly preferred. The organic solvent may substantially consist of methanol.

In other cases, the organic extraction composition preferably comprises or consists of an alcohol/ketone mixture, preferably in a ratio by volume of from about 70:30 or 75:25 to about 85:15 or 90:10. In preferred cases, the organic extraction composition comprises a C1-4 alcohol and a C3-4 ketone mixture, in that ratio range. In particularly preferred cases, the organic extraction composition comprises of a methanol/acetone mixture, in that ratio range. Most preferably, the organic extraction composition consists of a methanol/acetone mixture in a ratio by volume of from about 70:30 or 75:25 to about 85:15 or 90:10. These mixtures are particularly preferred because they effectively extract a diverse range of lipid classes which have different polarities (including cationic and anionic phospholipids, and neutral lipids), whilst minimising spectral noise and allowing reproducible spectra to be obtained.

Alternatively, the organic extraction composition comprises more than 50 vol % ether, preferably at least about 55 vol %, 60 vol %, 70 vol %, 80 vol % or 90 vol %. $C_{1-4}$ ethers are preferred (by which we mean, the carbon chain on either side of the ether linkage contains a between 1 and 4 carbons). Preferably the ether volume comprises or consists of diisopropylether (DIPE). The ether-based organic extraction composition may additionally comprise alcohols, ketones and/or esters, or mixtures thereof.

Data Gathering

The method of any aspect of the invention may further comprise after step (b) and after step (ci) or (cii) if present,
(d) a data gathering step, in which data representative of the extracted oxidised phospholipids is obtained.

The data may be obtained by mass spectrometry, which in turn may be MALDI-based.

MALDI is a quick and simple surface-analytical technique, allowing high-throughput of samples, an yielding robust and reproducible results. This makes it suitable for clinical application. In contrast to some other mass spectrometry ionisation techniques (e.g. ESI-MS) no further extraction steps of the analytes from the NP-surface are needed which allows direct ("on-probe") analysis. This makes for a simpler procedure.

MALDI-based analysis can use a positive or negative ionization mode.

A preferred case uses MALDI-QIT-TOF-MS/MS instrumentation for data analysis. This allows additional structural information about the NP-bound molecules to be obtained, improving the analysis accuracy.

For a system operating in the positive mode, 2,4,6-trihydroxyacetophenone (THAP) matrix is preferred for detection of neutral lipids like CEs. It is particularly preferred when doped with sodium (Na) or lithium (Li) acetate (ionisation promoters), which allow by formation of positively charged alkali adduct ions. The concentration range of the salt doping is preferably about 1-50 mM, preferably 10-20 mM. Doping at these levels allows complete suppression of other unwanted alkali counter ions (e.g. potassium) within the MALDI mass spectra.

6-aza-2-thiotymine (ATT) is a preferred matrix material when operating in the positive mode. This is particularly good for the detection of cationic phospholipids (e.g. phosphatidylcholines) and especially oxidised phospholipids (e.g oxidised phosphatidylcholines). ATT results in a softer ionization than other matrices used for lipid analysis (e.g. 2,5-DHB, THAP, etc.), and leads to less pronounced generation of fragmentation products, and so the resultant spectra are easier to analyse especially in regard to a quantitative evaluation of the mass spectra. It is particularly preferred when doped with (a) di-ammonium hydrogen citrate (DAHC), which suppresses the formation of mixed alkali adducts (e.g. Na or K) and allows for detection of exclusively protonated PLs and/or (b) guanidine-HCl (GUA), which considerably enhances the signal intensity of OxPLs. The concentration range of the salt doping is preferably about 1-10 mM, more preferably 1-5 mM for DAHC and 0.1-2 mM, preferentially 0.5-1 mM for GUA. Doping at these levels allows exclusive detection of protonated molecular ions within the MALDI mass spectra of OxPLs.

Note that ATT is preferred to THAP, because ATT can be used with ionising lasers which have a greater range of wavelengths (i.e. ATT is compatible with a greater range of lasers).

9-aminoacridine (9AA) is a preferred matrix material when operating in the negative mode. This is particularly good for the detection of anionic PLs and OxPLs or OxCEs derivatised to contain an anionic group (suitably carboxy group). In particular, 9AA doped with guanidine-HCl (GUA) or doped with a basic modifier such as pyridine (PYR) are particularly preferred, because the sensitivity of detection is increased and clear, reproducible spectra result. The concentration of GUA preferably comprises from about 3 mM or 4 mM to about 6 mM or 7 mM of guanidine, most preferably about 5 mM. The concentration of PYR preferably comprises about 0.3 vol % or 0.4 vol % to about 0.6 vol % or 1 vol % of pyridine, most preferably about 0.5 vol %.

In the above systems, the dopants (DAHC, GUA, PYR) each modulate the contribution of alkali salt adducts in the resultant mass spectra, and promote the detection of [M+H]$^+$ and [M−H]$^−$ ions in the positive and negative modes respectively.

In either mode, the sample preferably comprises the extracted nanoparticles and the matrix material. Preferably, the sample is prepared on a polymeric or plastics MALDI sample plate, rather than a conventional steel target. This minimises background noise especially in the low mass range (i.e. m/z<1000) where the majority of lipids are detected. For example, 48-well FlexiMass™-DS (Shimadzu) target slides can be used. Each of these features minimises the background noise, and improves the sensitivity of the method.

Data Analysis

The method of any aspect may additionally comprise
(e) a data analysis step, in which the oxidised lipids (suitably OxPLs) are detected, quantified, characterised and/or identified based on the data gathered.

Where MALDI-MS/MS is used in the data gathering step, peaks in the (fragment ion) spectrum can be used in the data analysis step to identify lipid (suitably phospholipid) headgroups and/or the composition of the (oxidized) fatty acid residues of the molecules.

The specific ratio of different oxidized lipids may be an indicator of a particularly degenerative condition (e.g. rancidification of food stuff), or a disease (i.e. pathological conditions related to oxidative stress).

In another aspect, the invention provides methods of diagnosis, comprising detecting and/or quantifying and/or identifying phospholipids in a biological sample according to the above methods.

Throughout this application, a percentage by liquid volume (vol %) is calculated based on the volume sum of the constituent elements prior to mixing.

Throughout this application, a reference to ALDO-OxPLs refers to OxPLs containing fatty acid residues with an aldehydic group. A reference to CARBO-OxPLs refers to OxPLs containing fatty acid residues with a carboxylic group. The same notation applies when referring to a different class of oxidised lipid, for example oxidised cholesterol ester OxCE. As an illustration, ALDO-OxPCs refers to oxidised phosphatidylcholines containing an aldehydic group and CARBO-OxPCs to oxidised phosphatidylcholines containing a carboxyl group.

Throughout this application, reference to "nano-MALDI" or the like refers to the method described herein for the first time. It includes all of the steps described herein. The invention should not be interpreted or limited to include all of these features. The invention is as defined in the claims.

BRIEF DESCRIPTION OF THE DRAWINGS

Embodiments of the invention will now be described in detail with reference to the accompanying figures, in which.

DETAILED DESCRIPTION

Figure 1:
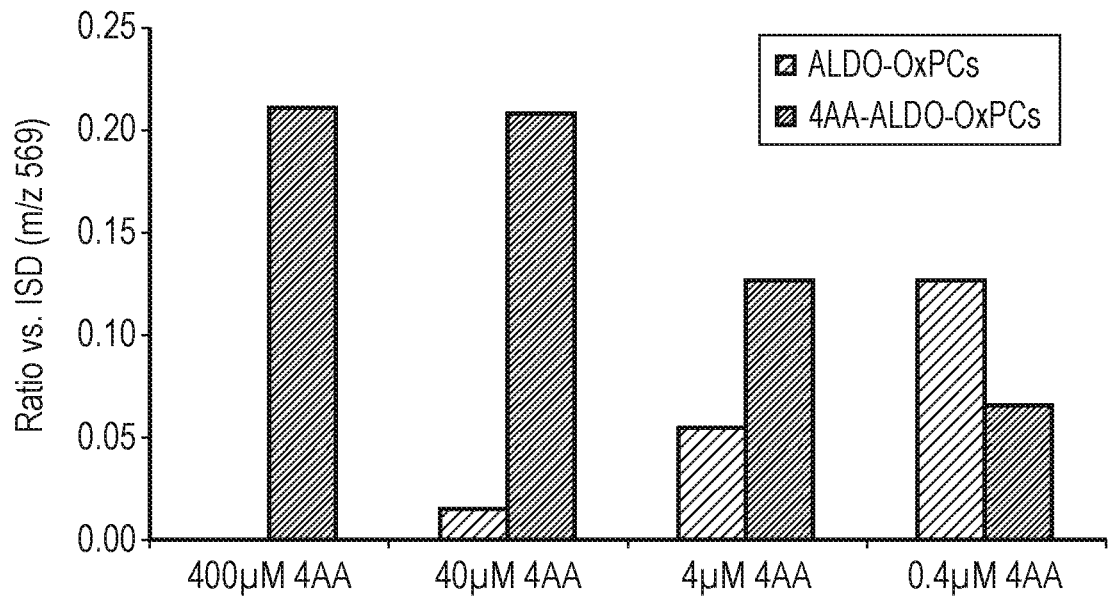
FIG. 1 shows the influence of the 4AA concentration on the MALDI ionization efficiency of 0.2 μM (~100 μg/μL) ALDO-OxPCs. The ATT matrix ion at m/z 569 was used as internal standard (ISD) for relative quantitative evaluation.

The embodiments described below are illustrative and by way of example only. They should not be taken to limit the scope of the invention in any way.

EXAMPLES

Methodology

Lipids

The lipids used in the experiments detailed below are listed in table 1.

Oxidation of Native PLs Containing Esterified PUFAs

Mixtures of short- and long-chain OxPLs (e.g. OxPAPC) derived from oxidation of the sn-2 PUFA residues of native PLs (e.g. PAPC) were obtained by auto-oxidation of completely dried samples at room temperature (25° C.) over night.

The samples were then re-suspended in chloroform and stored under argon at −80° C. until ESI-MS or MALDI-MS analysis.

Isolation and Modification of Human Low-Density Lipoprotein

Immediately after venipuncture blood was supplemented with EDTA (1 mM) and BHT (20 μM). Native LDL (n-LDL) was isolated from 3 mL human plasma by preparative ultracentrifugation (Sorvall ETD, SW-41 swing out rotor, 41000 rpm, 10° C., 24 h) using a discontinuous KBr density gradient.

For preparation of oxidized LDL (OxLDL) the EDTA-stabilized samples (0.25 mg/ml protein) were extensively dialyzed in the cold against PBS (pH 7.4). The samples were subsequently incubated
- with 50 μM $CuSO_4$ for 24 hours at 37° C. for preparation of Cu(II)-oxidized LDL (Cu-LDL) or
- with 8 mM NaOCl in 0.8 mM NaOH for the preparation of HOCl-oxidized LDL (HOCl-LDL).

Samples were stored under nitrogen in the dark at 4° C. to perform the subsequent experiments.

Lipid Extraction and Micro Solid-Phase Extraction of Mouse Plasma and Lipoproteins 500 μL MeOH was added to 20 μL of the samples, mixed vigorously for 1 minute and kept on ice for 30 minutes for lipid extraction. Afterwards, vials were centrifuged for 5 min (10000 rpm at +4° C.) to separate the lipids from the precipitated proteins. Finally, supernatants were carefully transferred to 2 mL glass vials and stored at −70° C. before further analysis.[20]

Before LC-ESI-MS/MS analysis, OxPLs were separated from bulk plasma lipids using our recently established micro-preparative high-performance solid-phase extraction (μHP-SPE) method.[7]

Briefly, C18-μSPE columns (PepClean, Pierce) were first equilibrated by 500 μL pure MeOH followed by an equal volume of MeOH:0.2% formic acid=70:30 (v/v) (=loading buffer). Afterwards the μSPE columns were loaded 3-times by the lipid extracts (dissolved in loading buffer) followed by a 500 μL washing step using loading buffer to remove most of the LPCs, followed by a single elution using 700 μL MeOH: 0.2% formic acid=82:18 containing the majority of OxPCs (>60-70%) and 800 μL MeOH:0.2% formic acid=98:2 containing >95% of the unoxidized PCs. The OxPC containing fraction was directly used for the subsequent LC-ESI measurements.

Derivatisation of Aldehydic OxPLs

Stock solutions containing 4 mM of the derivatisation reagents (2AA, 4AA, 4APA, GACA) and 8 mM sodium cyanoborohydride (CB) as reducing agent dissolved in MeOH were prepared. Additionally a stock solution of 4 mM 4-CBH in MeOH without the addition of CB was prepared.

2 μL of each of these solutions was mixed with 20 μL OxPLs dissolved in MeOH, or a 1:5-1:20 diluted mouse or human plasma lipid extract in MeOH, resulting in a final concentration of 400 μM of the labelling reagents in the sample.

Finally, the sample was incubated for 15 minutes at room temperature resulting in an almost complete reaction using 0.2 μM ALDO-OxPCs (see FIG. 1), which is below the normal physiological range reported in plasma.[21]

Nanoparticle Binding of OxPLs

Figure 2:
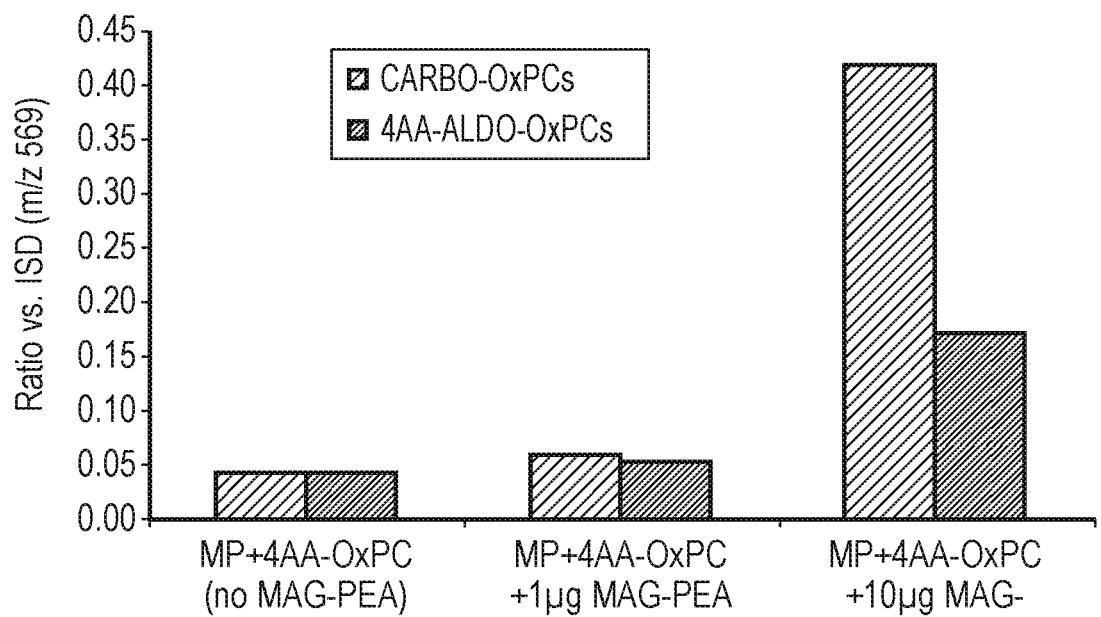
FIG. 2 shows the influence of different amounts (1 and 10 μg) of MAG-PEA-NPs on the binding of CARBO- and 4AA-ALDO-OxPCs (5 pg each) spiked to mouse plasma (MP). The ATT matrix ion at m/z 569 was used as internal standard (ISD) for relative quantitative evaluation.
Figure 3:
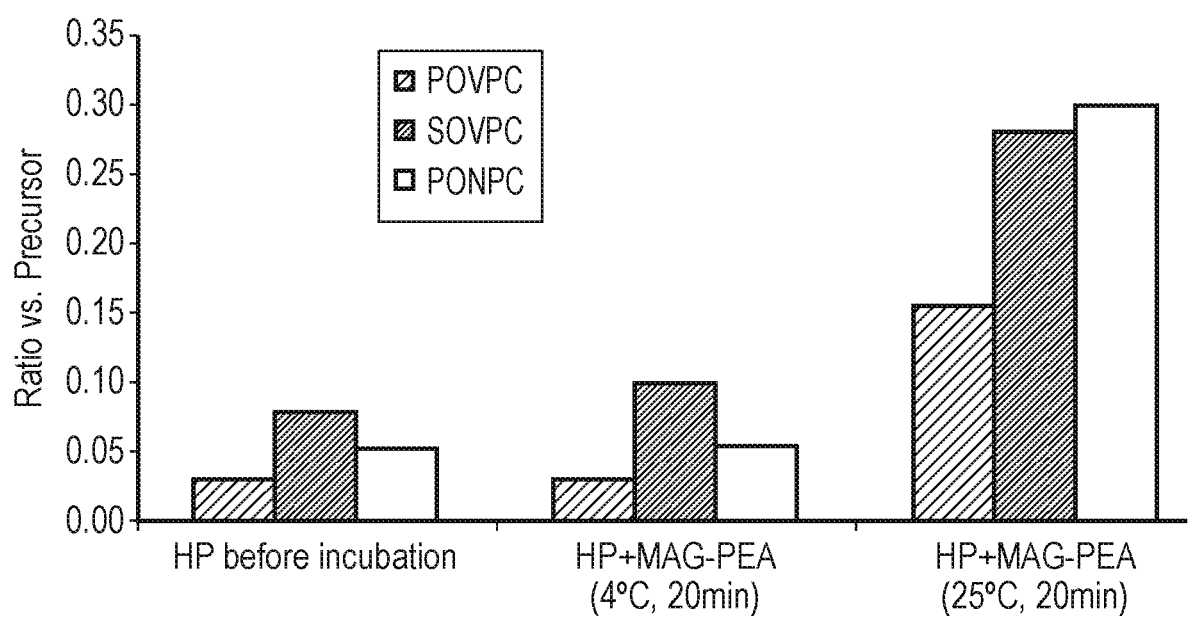
FIG. 3 shows the influence of different NP-incubation temperatures on the auto-oxidation of PLs. 20 μL human plasma (HP) lipid extracts dissolved in 200 μL MeOH were incubated with 20 μg MAG-PEA-NPs and incubated for 20 minutes at 4° C. and 25° C., respectively. The degree of oxidation was measured based on the signal intensity ratio of major ALDO-OxPLs (i.e. POVPC, SOVPC and PONPC) relative to their respective precursors (i.e. PAPC, SAPC and PLPC) detected by MALDI-MS.

For extraction of the OxPLs from solution, 20 μL of the lipid samples were mixed with 180 μL MeOH and 20 μg NPs were added. The solution was briefly mixed in order to suspend the NPs and incubated 20 minutes at 4° C. These were found the optimal conditions in regard to the binding efficiency and recovery of OxPLs without affecting their endogenous levels due to auto-oxidation of the samples during incubation (see FIGS. 2 and 3).

Subsequently, the NPs were sedimented by centrifugation (e.g. $ZrO_2$—NPs) or by using a magnet (e.g. $Fe_3O_4$—NPs), and the supernatant containing unbound material was removed.

Finally, the remaining NPs were washed by re-suspension in 500 μL MeOH, sedimented again and the supernatant discarded.

MALDI Sample Preparation

For the detection of OxPCs in positive ionisation mode (MALDI), the NPs were mixed with 2 μL ATT matrix (10 mg/mL) dissolved in EtOH:$H_2O$=90:10 (v/v) containing 2 mM GUA and 5 mM DAHC.[7]

For detection of OxPCs in the negative ionisation mode (MALDI), a 9AA matrix (10 mg/mL) dissolved in ISO:ACN=60:40 containing 5 mM GUA was used.[22] In either case, 1 µL of the NP-matrix suspension was deposited on FlexiMass™-DS (FLDS) sample plates (Shimadzu Biotech, Manchester, UK) and inserted into the MALDI instrument using a specific adaptor carrying up to four sample plates (AXIMA-Precision™, Shimadzu, Manchester, UK).

MALDI Mass Spectrometry

Mass spectra were obtained using an AXIMA-CFRplus (Shimadzu Biotech, Manchester, UK) curved-field reflectron time-of-flight (RTOF) mass spectrometer equipped with a 337 nm pulsed nitrogen laser (3-ns pulse width).

Measurements were performed either in positive or negative mode using delayed ion extraction for optimized mass resolution. The ion acceleration voltage was set to 20 kV and the reflectron analyzer was operated at 25 kV. The laser energy was adjusted to 5-10% above threshold irradiation. An integrated video imaging system (~25× magnification) allows direct observation of the sample spots under investigation.

A hybrid MALDI-quadrupole ion trap (QIT)-TOF mass spectrometer (AXIMA-Resonance, Shimadzu, Manchester, UK) was employed for recording of MS/MS spectra (mass range m/z 300-1000) based on low-energy collision-induced dissociation (CID) of the selected precursor ions using argon as collision gas[23]. The collision energy during the MS/MS experiments was adjusted to 100% precursor ion suppression.

In MS mode 300-500 single laser shots were accumulated. In MS/MS mode 500-1000 single laser shots were accumulated. An external calibration was performed, based on the exact mass values of the $[M+H]^+$ and $[M-H]^-$ ions using mixtures of the defined PL standards.

ESI Mass Spectrometry

ESI mass spectra were acquired using a 4000 QTrap triple quadrupole linear ion trap hybrid mass spectrometer equipped with a Turbo V electrospray ion source (Applied Biosystems, Foster City, Calif., USA).

The lipid samples were dissolved in 50 µl of methanol/UHQ 85:15 (v/v) containing 5 mM ammonium formate and 0.1% formic acid.

For LC-MS analysis 5-10 µL were injected onto a coreshell type C18 column (Kinetex 2.6 µm, 50×3.0 mm ID; Phenomenex, Torrance, Calif., USA), which was kept at 20° C. A linear binary gradient consisting of 5 mM ammonium formate and 0.1% (v/v) formic acid in UHQ (eluent A) and MeOH (eluent B) was used as mobile phases at a flow rate of 400 µL/min over 20 min total run time.

The ion source was operated in positive ion mode using an electrospray ionization voltage of 4500 V and an ion source temperature of 550° C. Nitrogen was used as nebulizer, heater, curtain, and collision gas for MS/MS experiments. Detection was carried out by selected reaction monitoring (SRM) of the m/z 184 product ion corresponding to the PC headgroup.

MS Data Analysis

MS data were processed by the manufacturer supplied instrument software versions Launchpad 2.9.1 (Shimadzu, Manchester, UK) and Analyst 1.5 (Applied Biosystems), respectively. MALDI mass spectra were routinely calibrated using the exact mass values of the lipid standards and smoothed using Savitzky-Golay algorithm.

Results

Evaluation of Different NP-Types for Selective Detection of OxPLs

Metal-Oxide Nanoparticles

Metal-oxide ($MeO_2$) particles (e.g. $SnO_2$, $TiO_2$, $ZrO_2$) have been described previously for the selective analysis of phosphopetides by MALDI-MS for proteomics studies or for HPLC-ESI-MS/MS analysis of PLs[24][25][26].

The inventors have previously shown that such particles can be used for the selective analysis of oxidised phospholipids containing carboxy-groups.

Metal-oxide nanoparticles contacted with mixtures of abundant unoxidized PLs and short- and long-chain OxPLs (e.g. OxPAPC spiked mouse plasma), showed a preferential binding and enrichment of carboxy-group containing OxPCs (CARBO-OxPCs) (e.g. PGPC, PAzPC) but not aldehydic OxPCs (ALDO-OxPCs) (e.g. POVPC) and long-chain OxPCs (e.g. PEIPC). See FIGS. 4A, 4B and 5.

Figure 6:
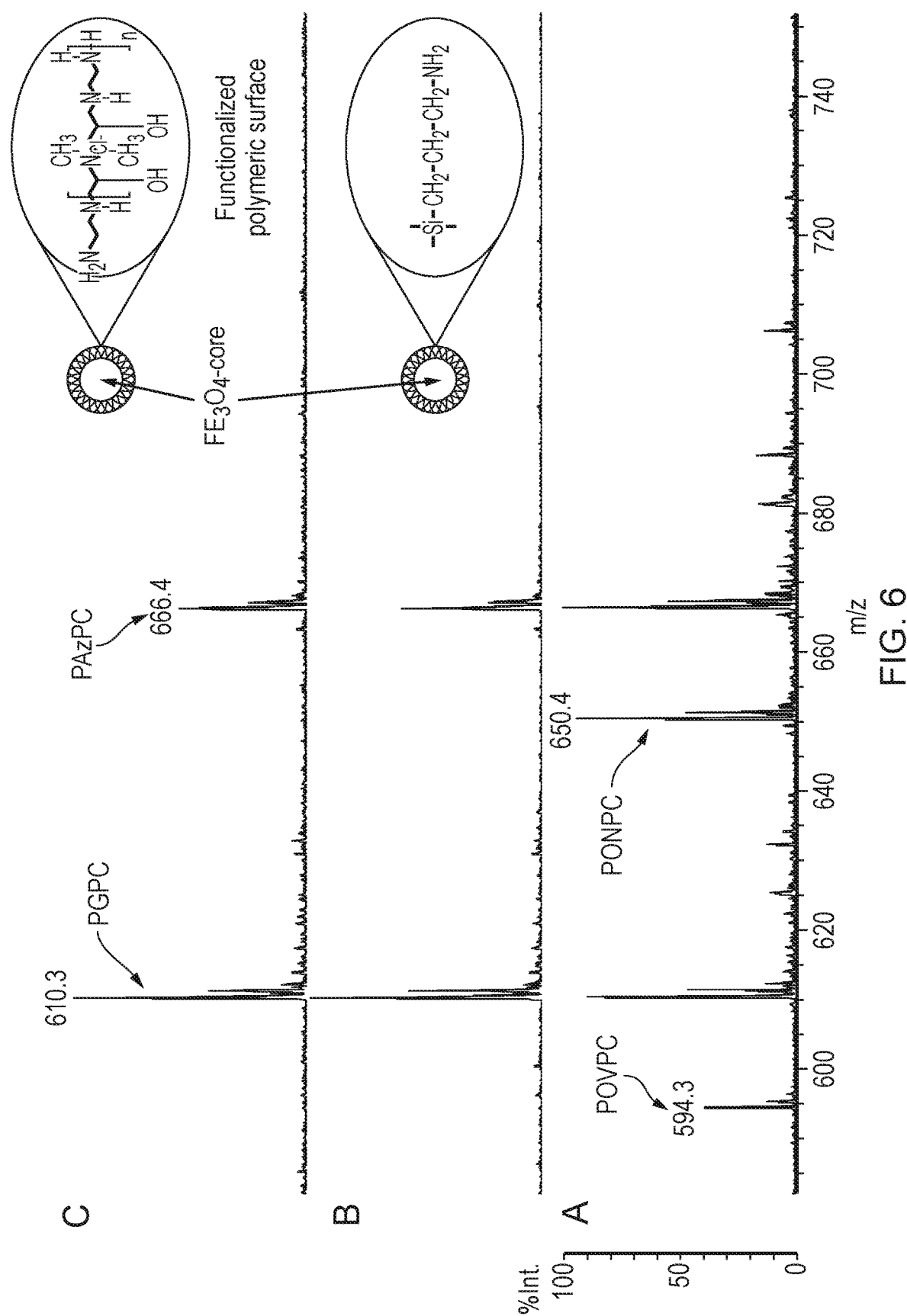
FIG. 6 illustrates the selective binding of CARBO-OxPCs using magnetic surface-functionalized $Fe_3O_4$—NPs (100 nm). In A) the MALDI mass spectrum of a mixture of four individual OxPCs (~200 µg/µL) before NP-binding is shown. The mass spectrum of the same sample recorded after incubation with B) aminopropyl-(MAG-$NH_2$) and C) polyetheramine-(MAG-PEA) functionalized NPs is shown. Note the selective NP-binding of the CARBO-OxPCs (i.e. PGPC, PAZPC) while the ALDO-OxPCs (i.e. POVPC, PONPC) were removed during the washing step.

The same enrichment effect of short-chain CARBO-OxPCs (e.g. PGPC) in contrast to "neutral" long-chain OxPLs (e.g. PEIPC) and the abundant unoxidized PLs (e.g. PLPC) was observed when OxPAPC-spiked mouse plasma samples were used (see FIG. 6).

Without wishing to be bound by theory, it is believed that this selectivity relies on an "ion-pairing mechanism" based on the electrophilic interaction of the anionic OxPLs (e.g. CARBO-OxPLs) and the nanoparticle surfaces.

Figure 7A:
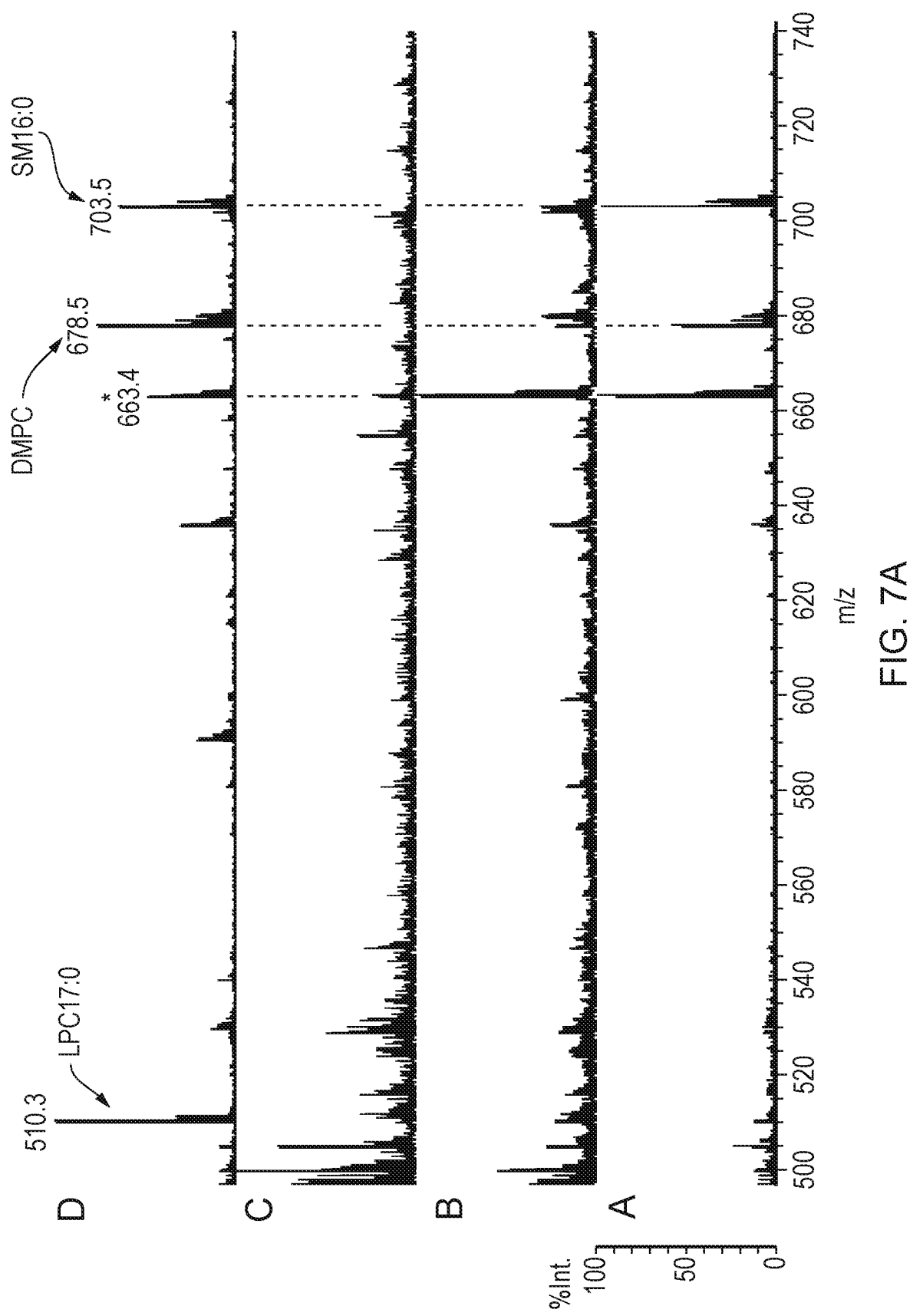
FIG. 7A shows MALDI spectra of PLs in the positive ionization mode using different types of 5000 nm $MeO_2$-microparticles (MPs). The MALDI mass spectra of A) a pure PL-standard mixture (~1 pmol/µL dissolved in MeOH) and after incubation with B) $TiO_2$-MPs, C) $SnO_2$-MPs, and D) $ZrO_2$-MPs are shown. Note that ATT was used as matrix substance. The signals represent $[M+H]^+$ ions of the individual PL species. The peak indicated by an asterisk (m/z 663) represents the $[M+H]^+$ ion of a plasticizer (Irganox®168) that leached out of the plastic materials used.
Figure 7B:
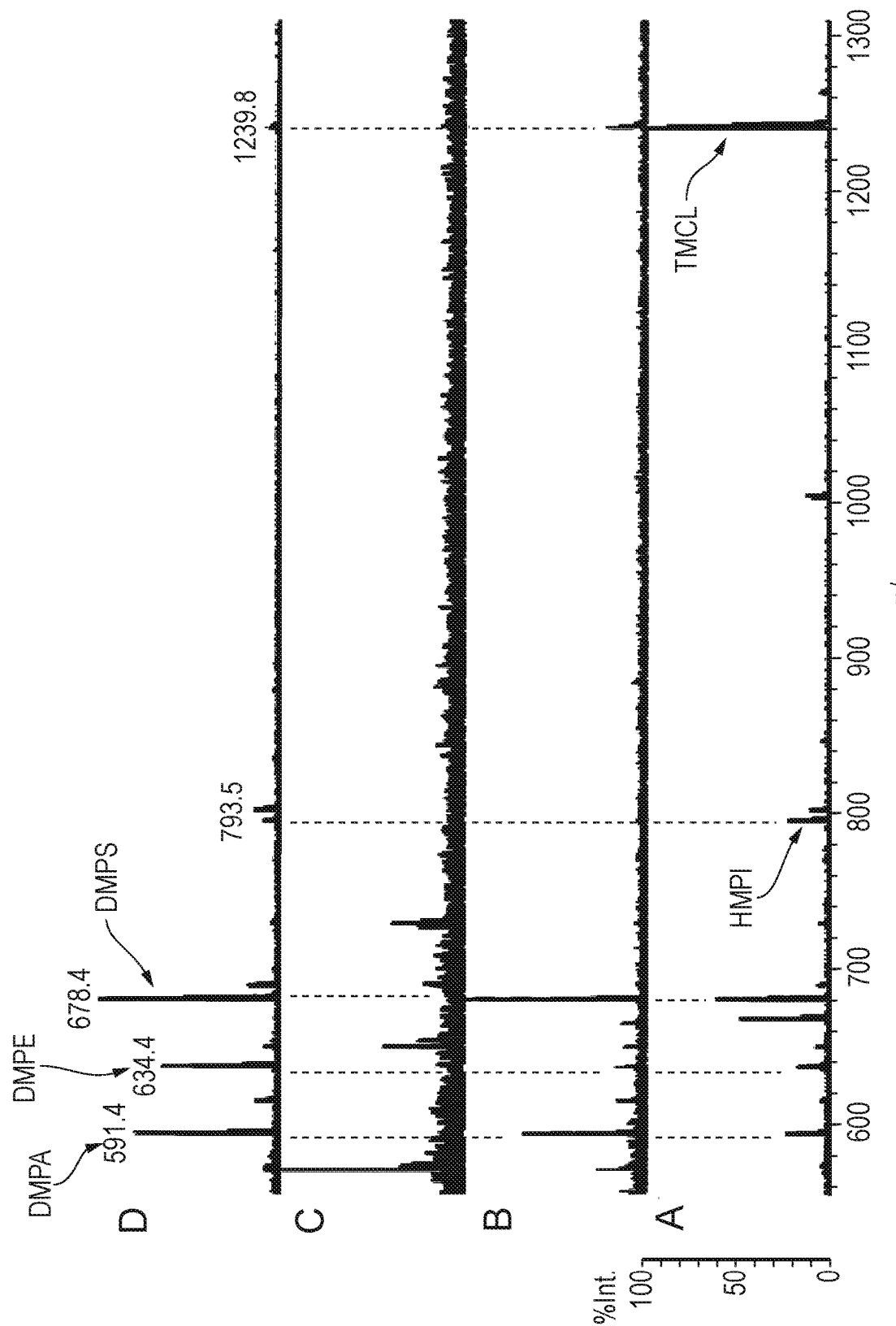
FIG. 7B shows MALDI spectra of PLs in the negative ionization mode using different types of 5 µm $MeO_2$-microparticles (MPs). The MALDI mass spectra of A) a pure PL-standard mixture (~1 pmol/µL dissolved in MeOH) and after incubation with B) $TiO_2$-MPs, C) $SnO_2$-MPs, and D) $ZrO_2$-MPs are shown. Note that 9AA was used as matrix substance. The signals represent $[M-H]^-$ ions of the individual PL species.

Further, the inventors have found that, of the metal oxide nanoparticles tested, that only $ZrO_2$ particles allowed the binding and detection of PLs from mixtures in positive (+) and negative (−) MALDI ionization mode (see FIGS. 7A and 7B). As can be clearly seen $ZrO_2$ particles show a preferred binding of acidic (anionic) PLs (e.g. PA, PE, PS) from a lipid mixture (FIG. 7B). Nevertheless some contribution of the phosphate headgroup to the binding in case of LPC, PC and SM cannot be ruled out using this type of particles (Figure A).

Magnetic Core Nanoparticles

Although $ZrO_2$—NPs were found to bind OxPLs well, the inventors found that they are sometimes unstable in solution, and needing repeated vortexing during sample incubation.

In contrast, so-called "magnetic-core" NPs (e.g. silanized iron oxide, carbon-coated cobalt) have been shown to be very suitable for sample handling and NP-harvesting using magnetic separation.[27][28]

The inventors tested the selectivity of nanoparticles comprising a magnetic iron oxide ($Fe_3O_4$)-core, surface functionalised with hydrophilic polymers. The hydrodynamic diameter of the nanoparticles is approximately 100 nm. The surface layer was believed to be approximately 10-60 nm thick.

Two nanoparticles types were tested. Each had a superparamagnetic magnetite ($Fe_3O_4$) core surrounded by an aminosilane matrix. One was surface-functionalized with propylamine (MAG-NH2) and the other with poly-(dimethylamin-co-epichlorhydrin-co-ethylendiamin) (MAG-PEA) respectively. These groups were selected for their anion exchange properties, and showed the same selectivity for CARBO-OxPCs (see FIG. 6). In contrast, to $MeO_2$ particles (e.g. $ZrO_2$) the contribution of the phosphate group for binding can be ruled out, as is demonstrated by the complete absence of signals related to POVPC and PONPC (FIG. 6). This further supports the electrophilic interaction binding hypothesis described above.

In contrast, to gold nanoparticles (GNPs) and also the $MeO_2$—NPs, the $MAG-NH_2$ and particularly the MAG-PEA nanoparticles showed full compatibility with ethanol, methanol or even acetone. This allows the analysis of OxPLs by MALDI-MS directly from lipid solutions extracted using these solvents (see Table 2).

TABLE 2

|  | H$_2$O | MeOH | EtOH | AcOH |
|---|---|---|---|---|
| GNPs | + | − | − | − |
| MeO$_2$-NPs | + | + | +/− | − |
| NH$_2$-NPs | + | + | + | − |
| PEA-NPs | + | + | + | + |

Stability of different NP-types in solvents used for lipid extraction of biological samples (e.g. mouse and human plasma).
GNPs: gold-NPs,
MeO2: metaloxide NPs,
NH2-NPs: aminpropyl-NPs,
PEA-NPs, polyetheramine-NPs.
MeOH: methanol,
EtOH: ethanol,
AcOH: acetone.

Comparison of Different Nanoparticle Binding Efficiency

Following these initial tests, methanolic lipid extracts of mouse plasma (MP) were spiked with OxPC-mixtures (e.g. OxPAPC) or defined OxPC standards (i.e. POVPC, PGPC, PONPC, PAzPC) at very low concentrations (~1-5 μg/A) and directly (i.e. "on-probe") analyzed by MALDI-MS.

Figure 4:
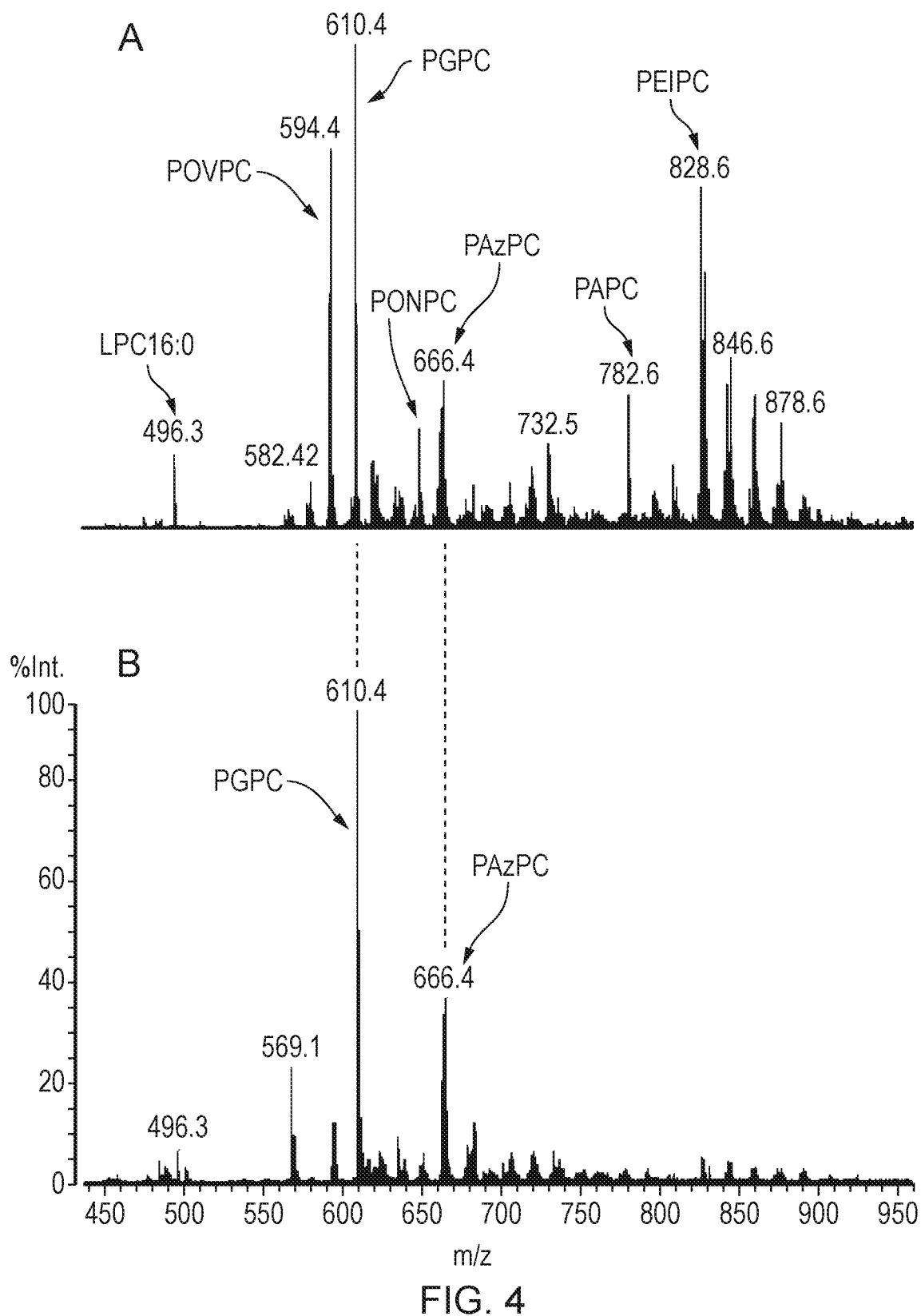
FIGS. 4A and 4B show the preferential binding of $ZrO_2$ nanoparticles to carboxy-group containing OxPLs, over aldehydic OxPLs and long-chain OxPCs. In A) the MALDI mass spectra recorded from a mixture of OxPLs before and in B) after incubation with $ZrO_2$—NPs are shown.
FIGS. 4C and 4D show the effect of the nanoparticle identity on MALDI ionisation properties and binding efficiencies. In C) the influence of ZrO2 and two surface-functionalize $Fe_3O_4$-core NPs (i.e. MAG-NH2 and MAG-PEA) on the ionization and in D) the trapping efficiency of individual short-chain OxPCs (5 pg each) spiked to mouse plasma (MP) is shown. The ATT matrix ion at m/z 569 was used as internal standard (ISD) for relative quantification of the peaks.
Figure 4:
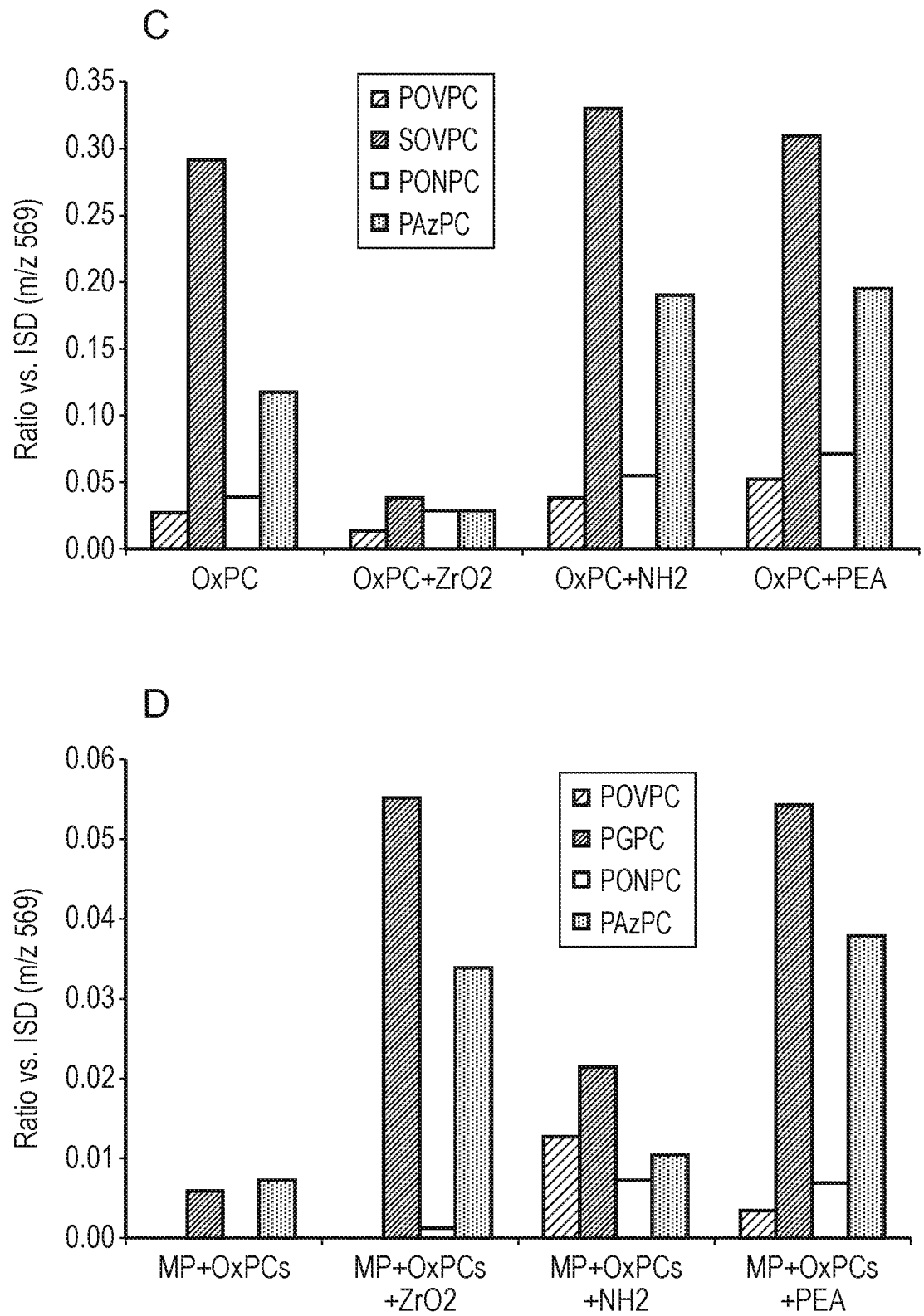
Figure 5:
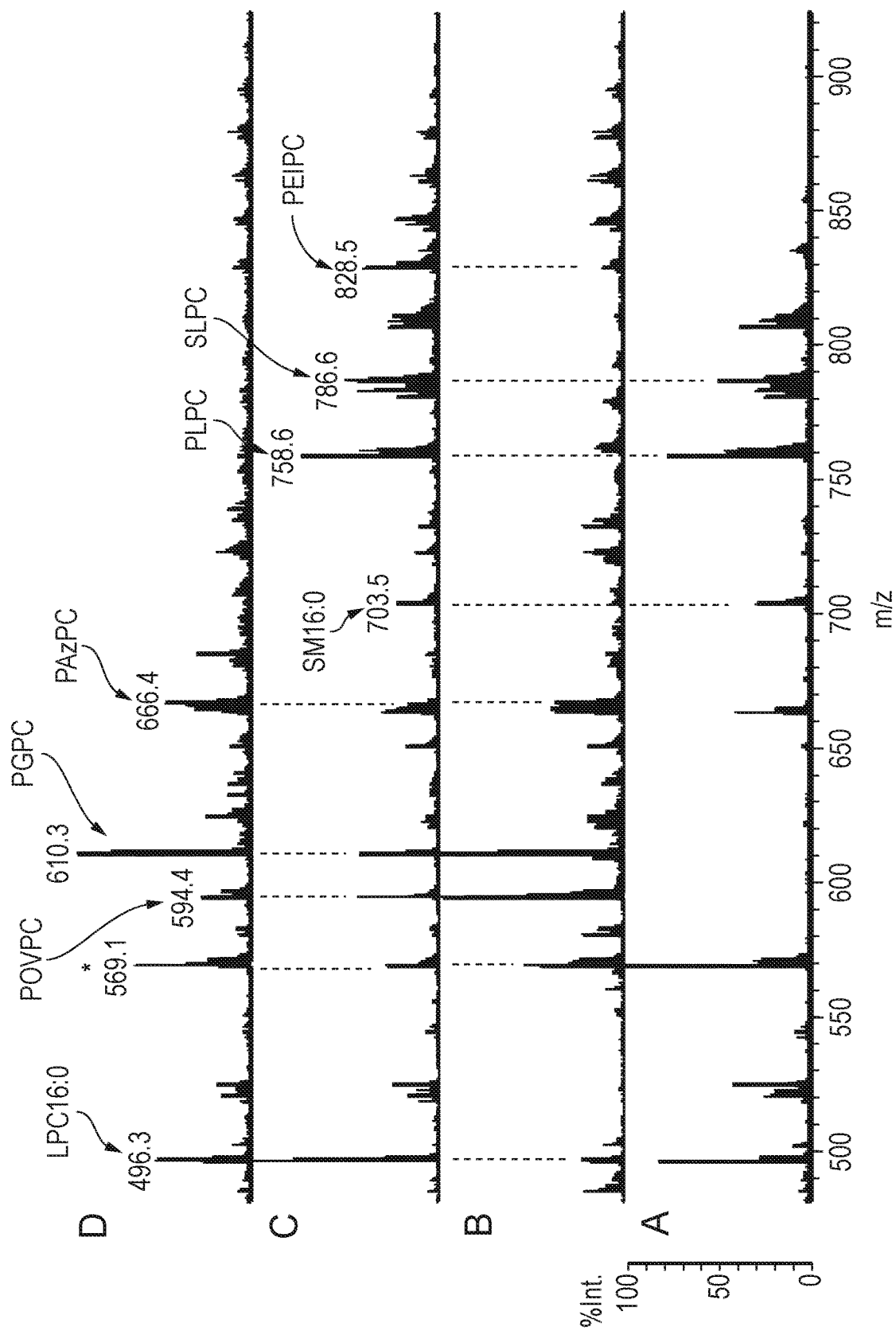
FIG. 5 illustrates the selective binding of OxPCs from human plasma (HP) using $ZrO_2$—NPs (100 nm). MALDI mass spectra of A) pure HP, B) pure OxPAPC (~10 ng/μL) and C) a mixture of HP+OxPAPC dissolved in MeOH are shown. In D) the MALDI mass spectrum of the mixture shown in C) but after incubation with 10 µg $ZrO_2$—NPs and on-probe analysed by MALDI-MS is shown. Note the selective binding of short-chain OxPCs (e.g. POVPC, PGPC, PAZPC) but absence of any other abundant PLs present in HP (e.g. PLPC, SM16:0). The peak indicated by an asterisk (m/z 569) originates from ATT matrix used for sample analysis.

The inventors have found that different NPs influence the MALDI ionization properties to different extents, and that different NPs have quite different binding efficiencies (see FIGS. 4C and 4D). Using defined amounts of OxPC standards and of nanoparticles for incubation, the figures in Table 3 were determined.

TABLE 3

| ZrO2 | MAG-NH2 | MAG-PEA | |
|---|---|---|---|
| 3.3 | 2.9 | 3.8 | pg OxPCs/10 μg NPs on target |
| 65.9 | 58.6 | 77.0 | Recovery (%) |
| 0.53 | 0.47 | 0.62 | fmol OxPCs/μg NPs |
| not specified | ~2 × 10$^9$ | ~2 × 10$^9$ | NPs/μg (according to the manufacturer) |
| — | 1.41 × 10$^{-1}$ | 1.85 × 10$^{-1}$ | Molecules OxPC/NP |
| ~0.2 nmol/L | ~0.2 nmol/L | ~0.2 nmol/L | OxPC conc. of the samples |

Experimental figures for different NPs for the detection of OxPLs by MALDI-MS. A mixture of 0.125 pg OxPCs/μL (~0.2 nmol/L) dissolved in MeOH was used for evaluation. The total amount of OxPCs (in pg/10 μg NPs) was determined based on comparison of the signal intensity of individual OxPCs measured on-probe before and after NP-binding.

The OxPC recovery rate based on comparison of the individual signal intensity of the peaks from an equimolar OxPC mixtures measured on-probe together with the different NPs before and after incubation was found to be 59-77%.

The number of OxPC molecules bound per NP was found to be ~1.6×10$^{-1}$ for MAG-NH2 and MAG-PEA. This was sufficient to detect and quantify OxPLs at a sample concentration of ~0.2 nmol/L (=200 pM) representing a 3-4 orders of magnitude higher sensitivity than the physiological concentrations of OxPLs in human or animal plasma (~2 nmol/L-6 μmol/L)[29][30][31].

In summary, based on this careful evaluation the suitability of NPs for the selective detection of OxPLs by MALDI-MS was found in the following order: MAG-PEA>ZrO$_2$>MAG-NH2.

Testing of Derivatisation Reagents for MS-Tagging and NP-Binding of OxPLs

The inventors have found that, while CARBO-OxPLs (e.g. PGPC, PAzPC) can be readily extracted using nanoparticles, ALDO-OxPLs (e.g. POVPC, PONPC) cannot (see for example, FIG. 6).

The inventors use chemical derivatisation in order to introduce a negatively charged chemical group (e.g. a carboxyl group) into ALDO-OxPLs via chemical derivatisation of the ω-terminal aldehyde groups of the sn-2 FA residues. This allows capture of ALDO-OxPLs by nanoparticles with "electrophilic" surface properties, using the "ion-pairing mechanism" described above.

Chemical derivatisation to aid in MALDI-MS analysis is known, as discussed above. The prior art strategies are intended to introduce specific mass shifts (i.e. "MS-tagging") and to use characteristic reporter ions allowing a better differentiation of oxidized lipid molecules containing carbonyl-groups (i.e. aldehydes and/or ketones) from more abundant isobaric unoxidized lipid species. Another method[13] uses 2,4-Dinitrophenylhydrazine (DNPH) as a reactive matrix for the analysis of OxPLs by MALDI-MS to allow the detection of small volatile aldehydes as hydrazones without the need for an additional MALDI matrix.

In contrast, the inventors' method improves in detection/analysis by
a) mass-tagging the derivatised aldehydes,
b) improving the ionization efficiency of the OxPLs, and
c) allowing nanoparticle enrichment of the OxPLs.

The method allows direct ("on-probe") analysis of the nanoparticles by MALDI-MS.

Comparison of Reagents

Figure 8:
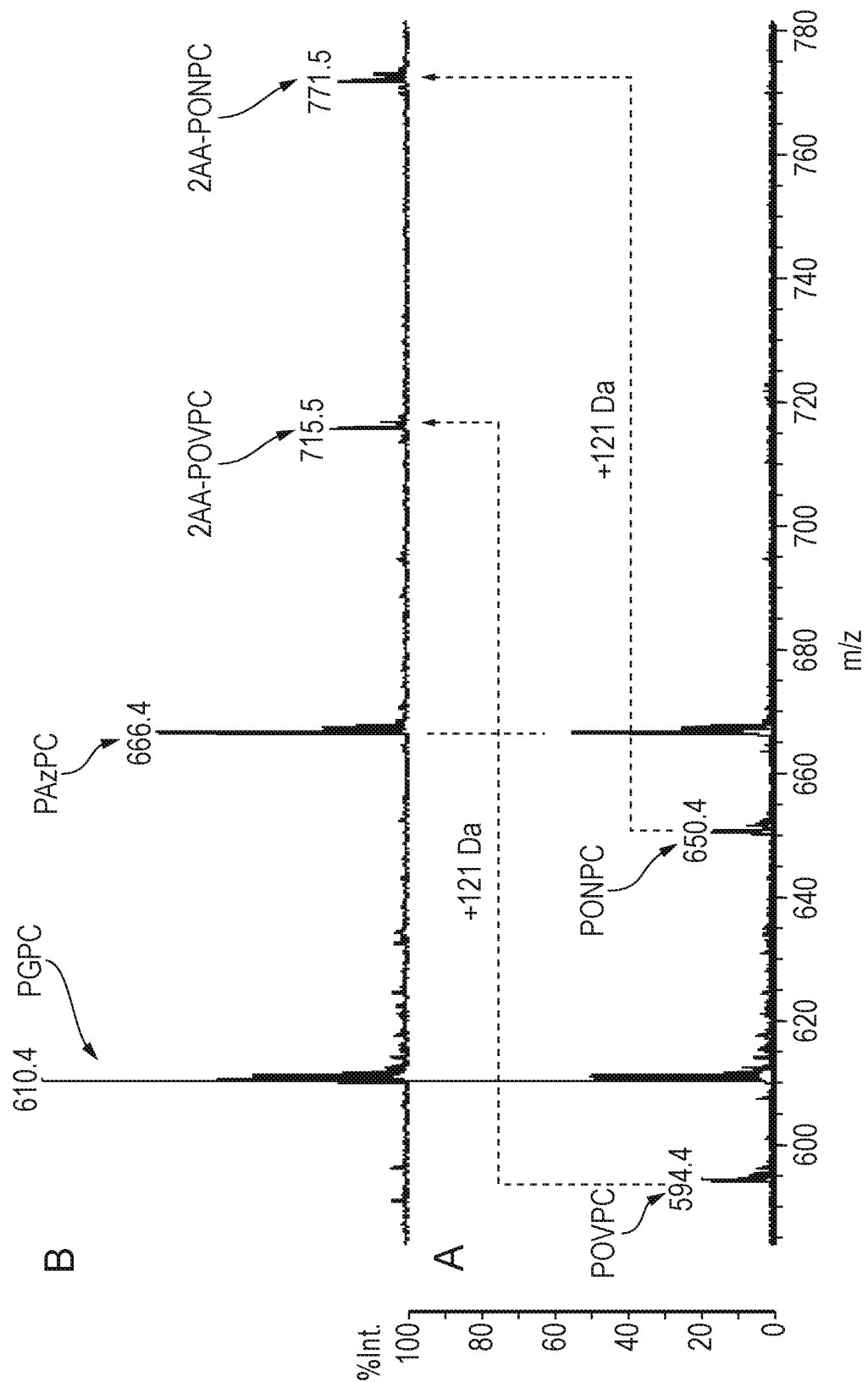
FIG. 8 demonstrates the selective derivatisation of ALDO-OxPCs using 2-aminoantranilic acid (2AA). The MALDI mass spectra of A) a mixture of four individual OxPCs (~50 µg/µL) and B) of the same sample after derivatization with 2AA reagent are NP-binding, are shown. Note the mass shift of 121 Da of the ALDO-OxPCs (i.e. POVPC, PONPC) while the m/z values of the CARBO-OxPCs (i.e. PGPC, PAZPC) remain unaffected.
Figure 9:
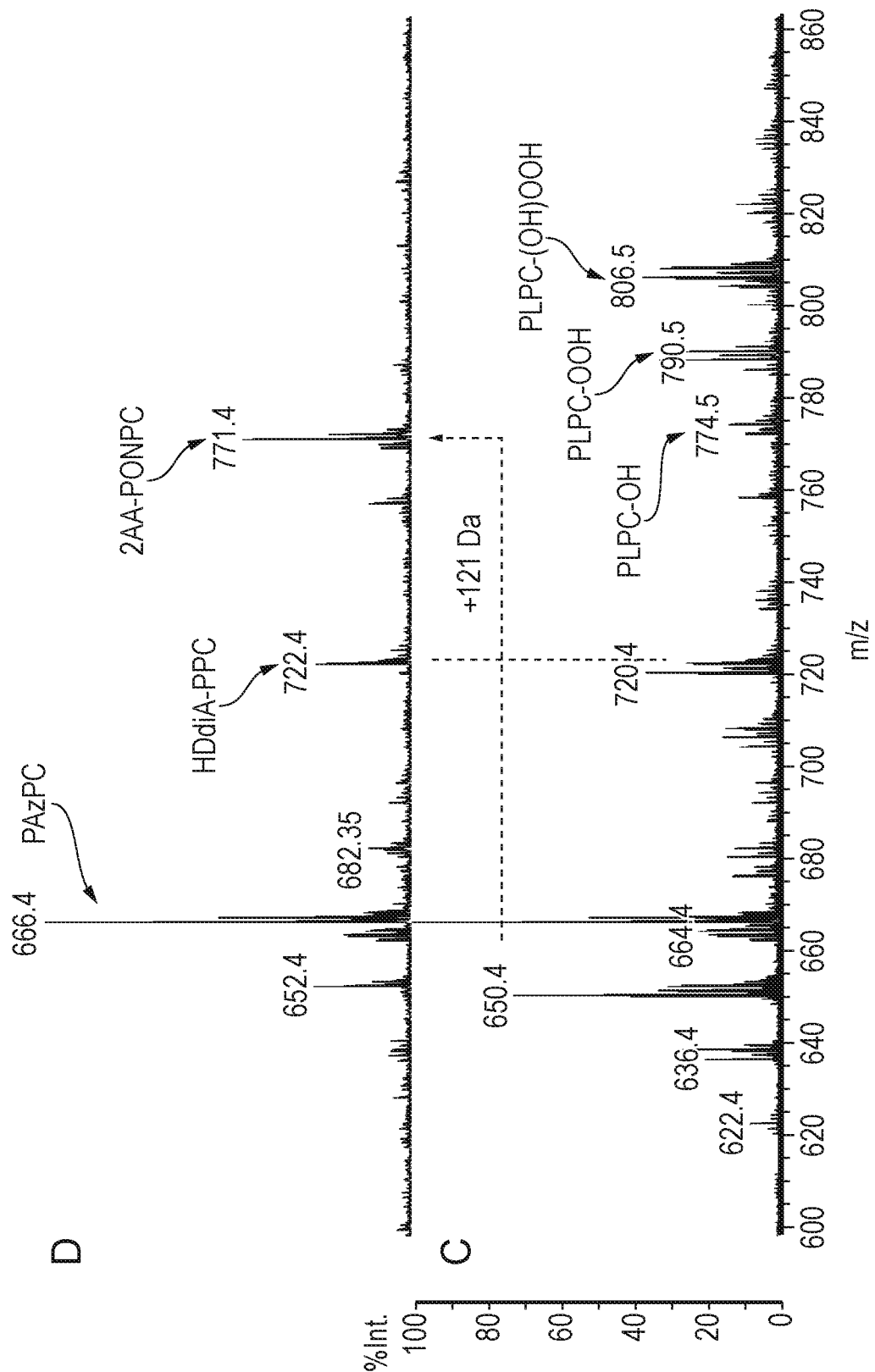
FIG. 9 demonstrates selective 2AA-derivatisation and NP-binding of ALDO-OxPCs from mixtures of lipid oxidation products. The MALDI mass spectra of ~10 ng/µL A) OxPAPC and C) OxPLPC before and B) OxPAPC and D) OxPLPC after 2AA-labeling and binding to MAG-NH2-NPs are shown. Note the selective NP-binding of CARBO-OxPCs and 2AA-labeled ALDO-OxPCs, while long-chain OxPLs (i.e. lipid hydroperoxides and epoxyisoprostanes) are removed during the washing step. The mass shift of 121 Da after 2AA-derivatization is indicated for major ALDO-OxPCs present in the samples. The peak indicated by an asterisk (m/z 569) originates from ATT matrix used for sample analysis.
Figure 9:
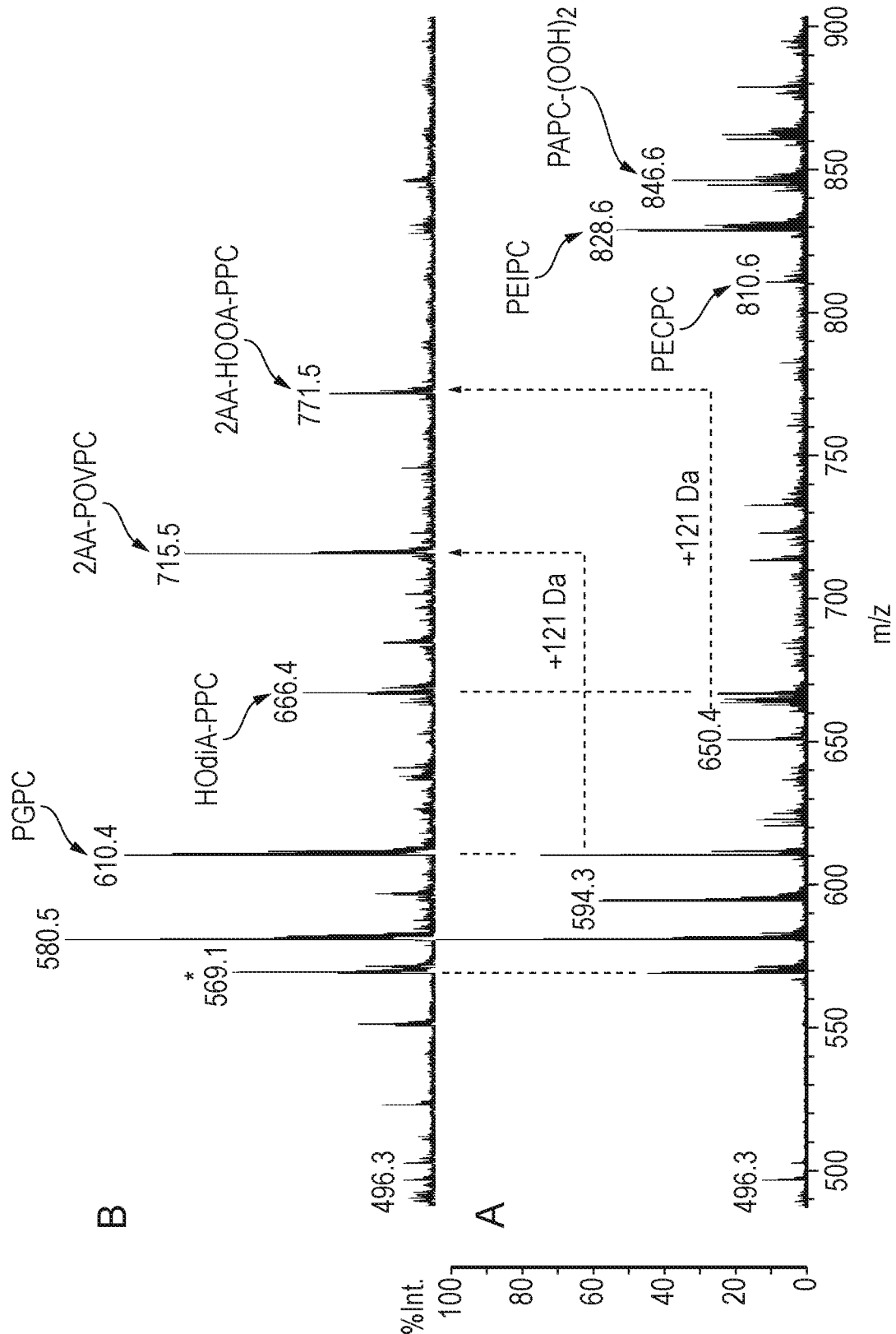

One example of the derivatisation method reacts 2AA with ALDO-OxPLs in the presence of a reducing agent. This reaction introduces a carboxy-group to the OxPL allowing nanoparticle enrichment. It also introduces an aromatic group, which is readily ionisable in mass spectrometry analysis. Further, there is also a characteristic mass shift of 121 Da, allowing ready differentiation from CARBO-OxPLs (see FIGS. 8 and 9).

Other 2AA-derivatives were tested to determine their effect on the MALDI ionization efficiency and NP-binding of ALDO-OxPLs. When compared to 2AA;

the use of 4-AA was found to improve the signal intensity of ALDO-OxPLs (e.g. POVPC and PONPC) and increase the binding efficiency to the NPs (e.g. PEA-NPs);

the use of 4-APA was found to reduce the signal intensity and reduce the binding efficiency;

the use of 6-ACA, which has no phenyl group, was found to have no significant impact on the ionization efficiency but to dramatically reduce the NP-binding properties of ALDO-OxPLs.

Figure 10:
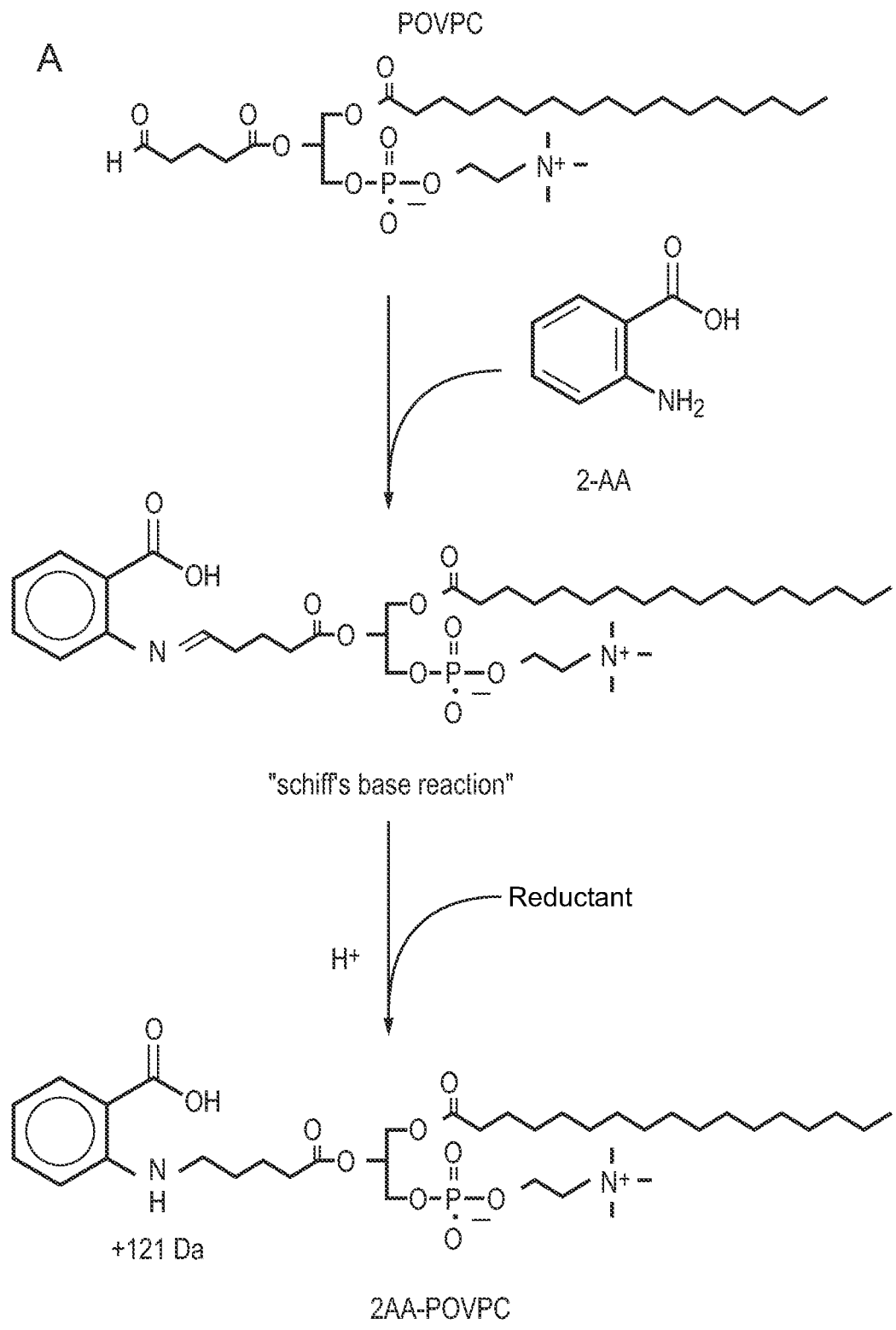
FIG. 10A shows the mechanism for derviatisation ("reductive amination") of an example aldehydic OxPC (POVPC), using a 2AA derivatisation reagent. The w-terminal carbonyl-group (i.e. the aldehyde) of the POVPC initially forms an intermediate Schiff's base (imine), which is subsequently reduced to the amine using a reducing agent (e.g. cynanoborohydride). The resulting mass shift of +121 Da can be used as specific "mass tag" during MALDI-MS analysis
FIGS. 10B and 10O show the results of the derivatisation procedure for four different derivatisation reagents. In B) the influence of different derivatization reagents on the ionization efficiency of different ALDO-OxPCs and in C) the binding efficiency to MAG-PEA-NPs compared to the unlabelled (pure) OxPCs are shown. The ATT matrix ion at m/z 569 was used as internal standard (ISD) for relative quantification of the peaks. 2AA: 2-aminoantranilic acid, 4AA: 4-aminoantranilic acid, 4APA: 3-(4-aminophenyl)-propionic acid, GACA: 6-aminocaproic acid
Figure 10:
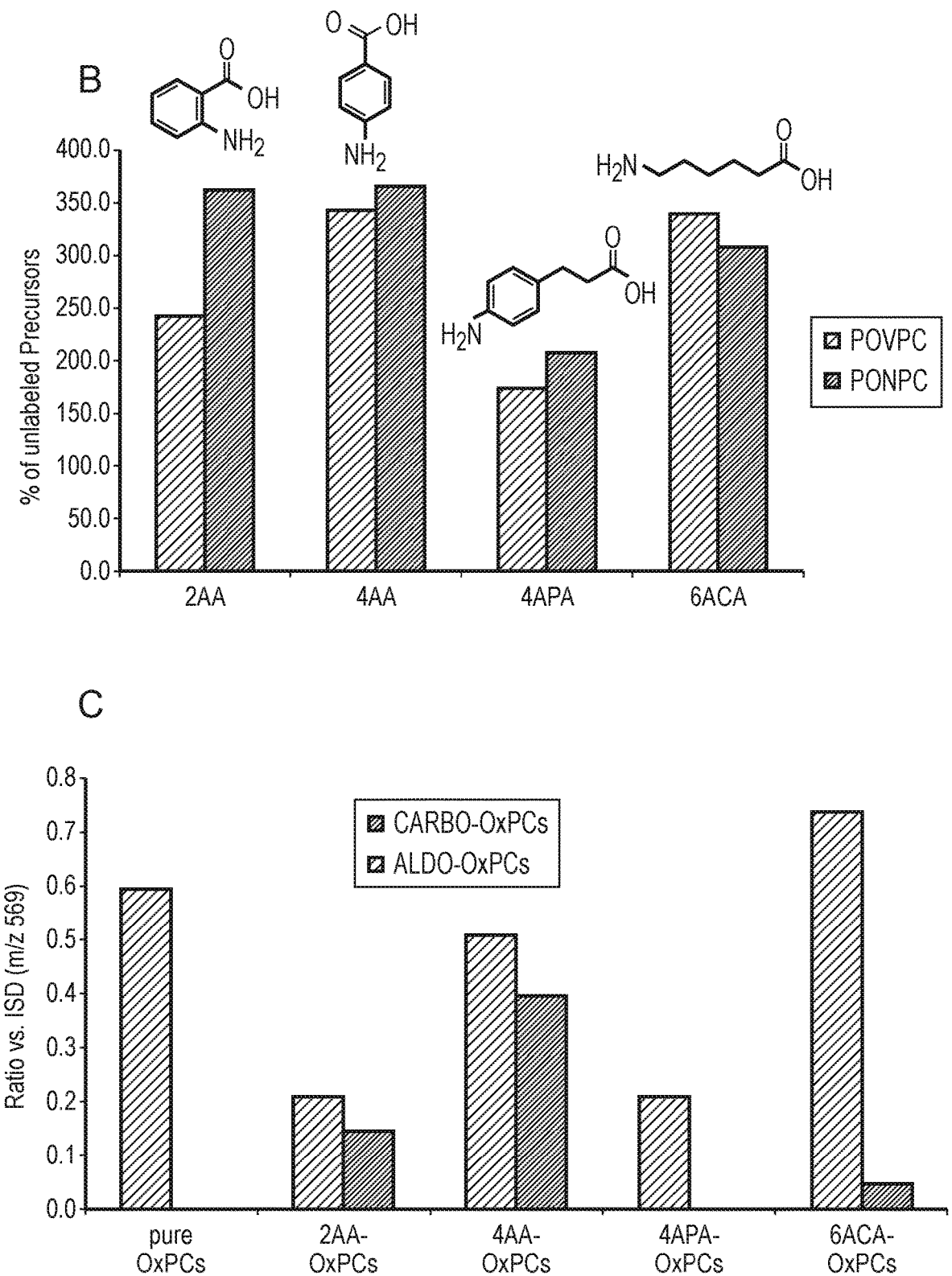

See FIGS. 10B and 10C.

These results clearly demonstrate the influence of the physico-chemical properties of the different labelling reagents (e.g. gas-phase basicity, and steric properties) on the MALDI process, as well as the importance of optimized stereochemistry for interaction with functional groups on the NP-surface.

Accordingly, the suitability of the derivatisation agents tested has been determined to be 4-AA>2AA>6ACA>4APA.

4-carboxybenzohydrazide (4-CBH) was also tested. This molecule was found to introduce a carboxy group to ALDO-OxPLs and additionally to α,β-unsaturated OxPLs containing no ω-terminal aldehydic groups (e.g. KDdiA-PC).

4-AA>2AA>6ACA>4APA all react by reductive amination. In contrast, 4-CBH reacts to form a hydrazine. 4-CBH provides comparative signal intensity and binding efficacy results as 4-AA, but allows analysis of additional oxidised lipids.

Concentration of Derivatisation Agent

The optimum 4AA-concentration has been found to be 20 µM 4AA in the incubation solution, which maximised binding of CARBO- and ALDO-OxPCs to MAG-PEA-NPs.

Signal quenching was observed at higher concentration (FIG. 11A), indicating saturation of the binding sites on the NP-surface by the excess, unreacted 4AA in the solution.

Figure 11:
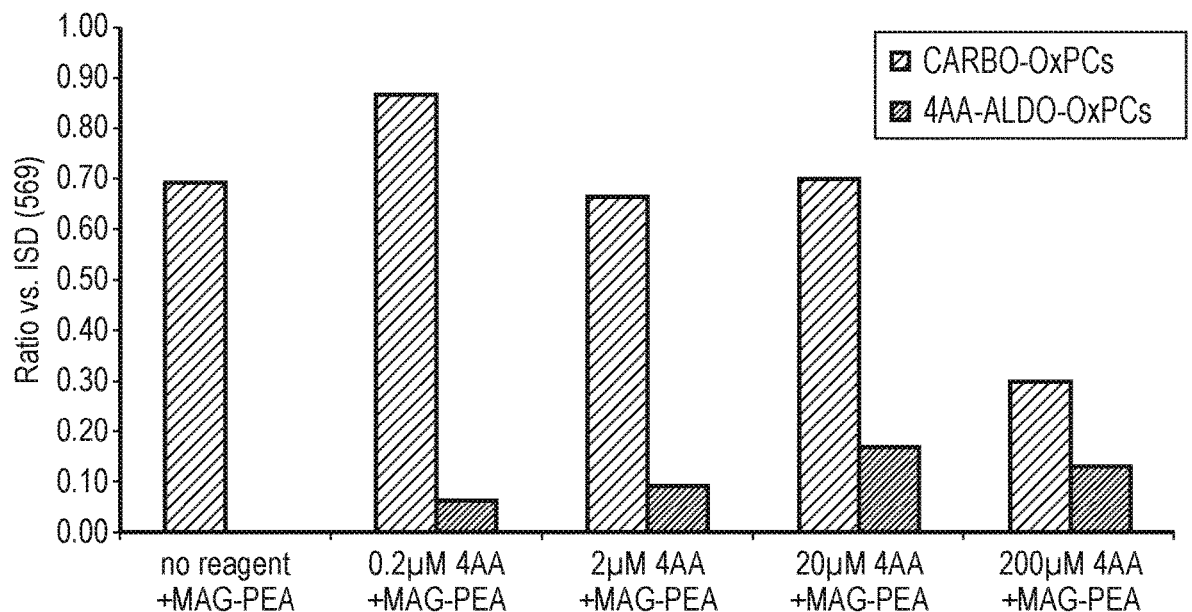
FIG. 11 shows the influence of the 4AA concentration on the OxPC-binding efficiency and the capacity of MAG-PEA-NPs. In A) the effect of increasing concentration of 4AA (0.2-200 µM) of CARBO- and 4AA-labeled ALDO-OxPCs on the binding to MAG-PEA-NPs and in B) the percentage of different amounts (0.4-20 nM) of CARBO- and 4AA-ALDO-OxPCs bound to ~20 µg MAG-PEA-NPs are shown. The ATT matrix ion at m/z 569 was used as internal standard (ISD) for relative quantitative evaluation.
Figure 11:
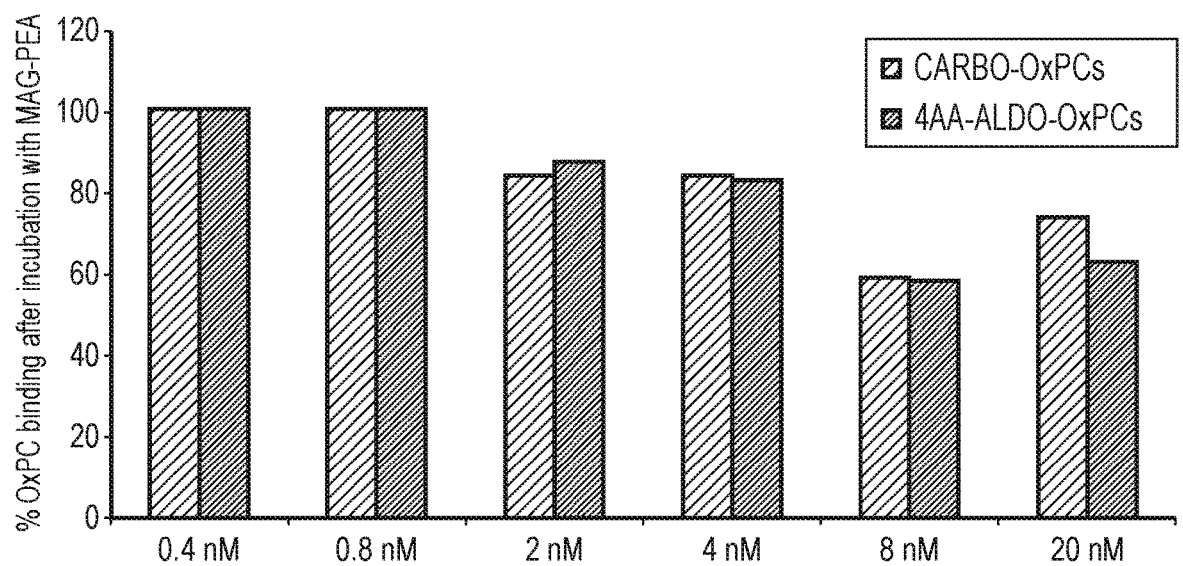

Thus, the surface capacity of ~20 µg MAG-PEA-NPs is sufficient to capture 80-100% of total OxPCs present at a concentration of ~0.4-4 nM in the incubation solution (FIG. 11B).

OxPL Profiling and Quantification from Mouse Samples

The suitability of MS/MS for the targeted detection of the NP-captured OxPLs was tested using MALDI-QIT-TOF- and ESI-MS/MS as reference methods.

Figure 12:
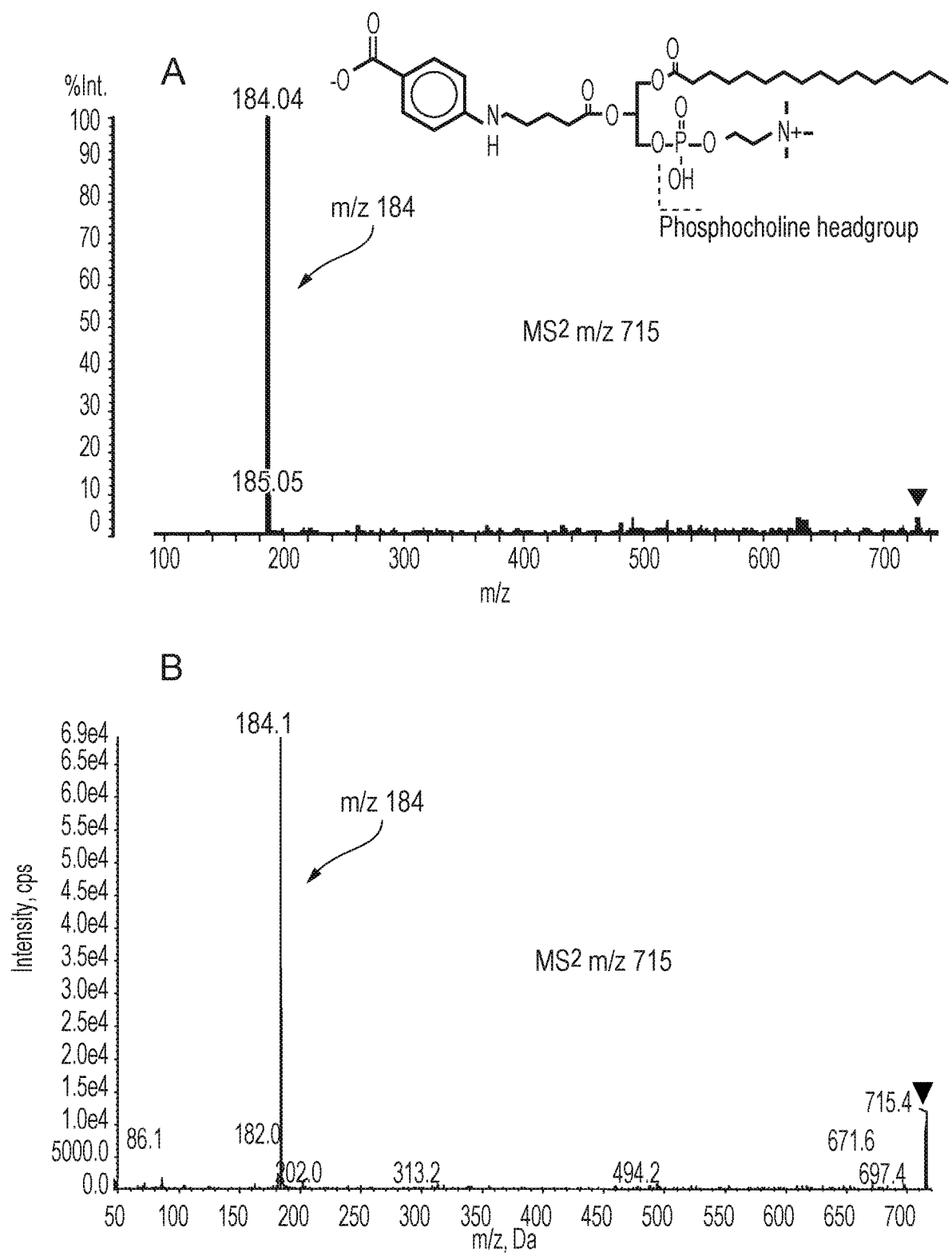
FIG. 12 shows the influence of 4AA-derivatization on the MS/MS properties and chromatographic behaviour of ALDO-OxPCs. In A) the MS/MS spectra of 4AA-POVPC (m/z 715) using MALDI-QIT-TOF and B) ESI-QQQ-MS/MS are shown. In C) the extracted ion chromatograms (EIC) of C) POVPC (m/z 594) and D) 4AA-POVPC (m/z 715) based on monitoring of the diagnostic ion at m/z 184 by LC-ESI-SRM-MS/MS are shown. A retention time shift of about 2.5 minutes and complete absence of the small isobaric peaks was observed after derivatisation. Note that the diagnostic fragment ion m/z 184 derived of the phosphocholine headgroup from 4AA-POVPC (m/z 715) is independent of the used ionization technique (i.e. ESI- or MALDI) and instrument types (i.e. QIT-TOF or QQQ).
Figure 12:
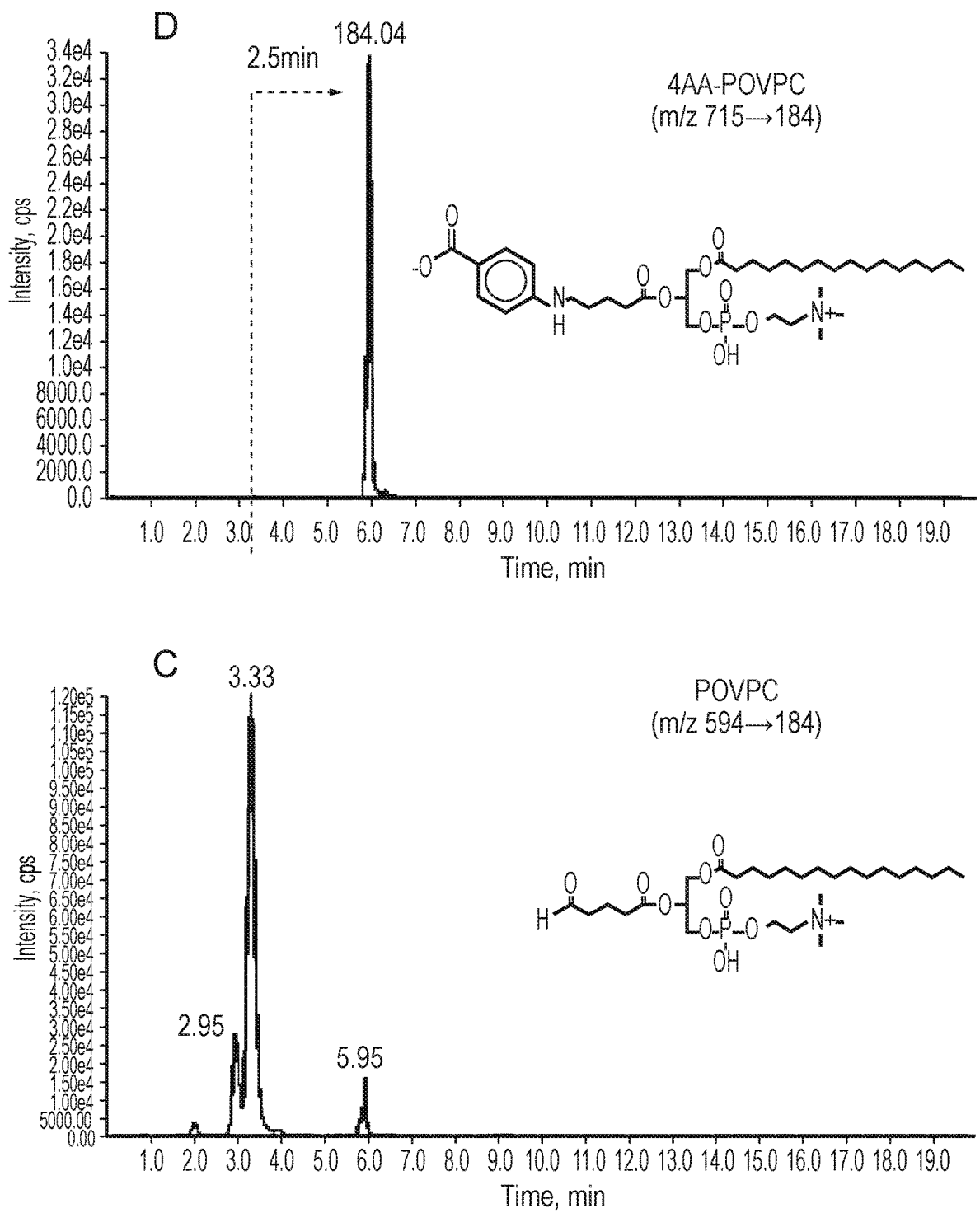

The MS/MS spectra of both the CARBO-OxPCs and 4AA-labeled ALDO-OxPCs showed only one predominant m/z 184 fragment ion derived from the PC headgroup (see FIGS. 12A and 12B). This was observed independent of the ionization process (i.e. MALDI or ESI) and the instrument type.

Moreover, the incorporation of 4AA into the sn-2 acyl-group of the molecules leads to a retention time shift (~2.5 minutes) of the peak at m/z 715 (4AA-POVPC) compared to the unlabeled POVPC at m/z 594 (see FIGS. 12C and 12D) which allows the chromatographic separation of the derivatised OxPC molecules from their unreacted precursors.

Figure 13:
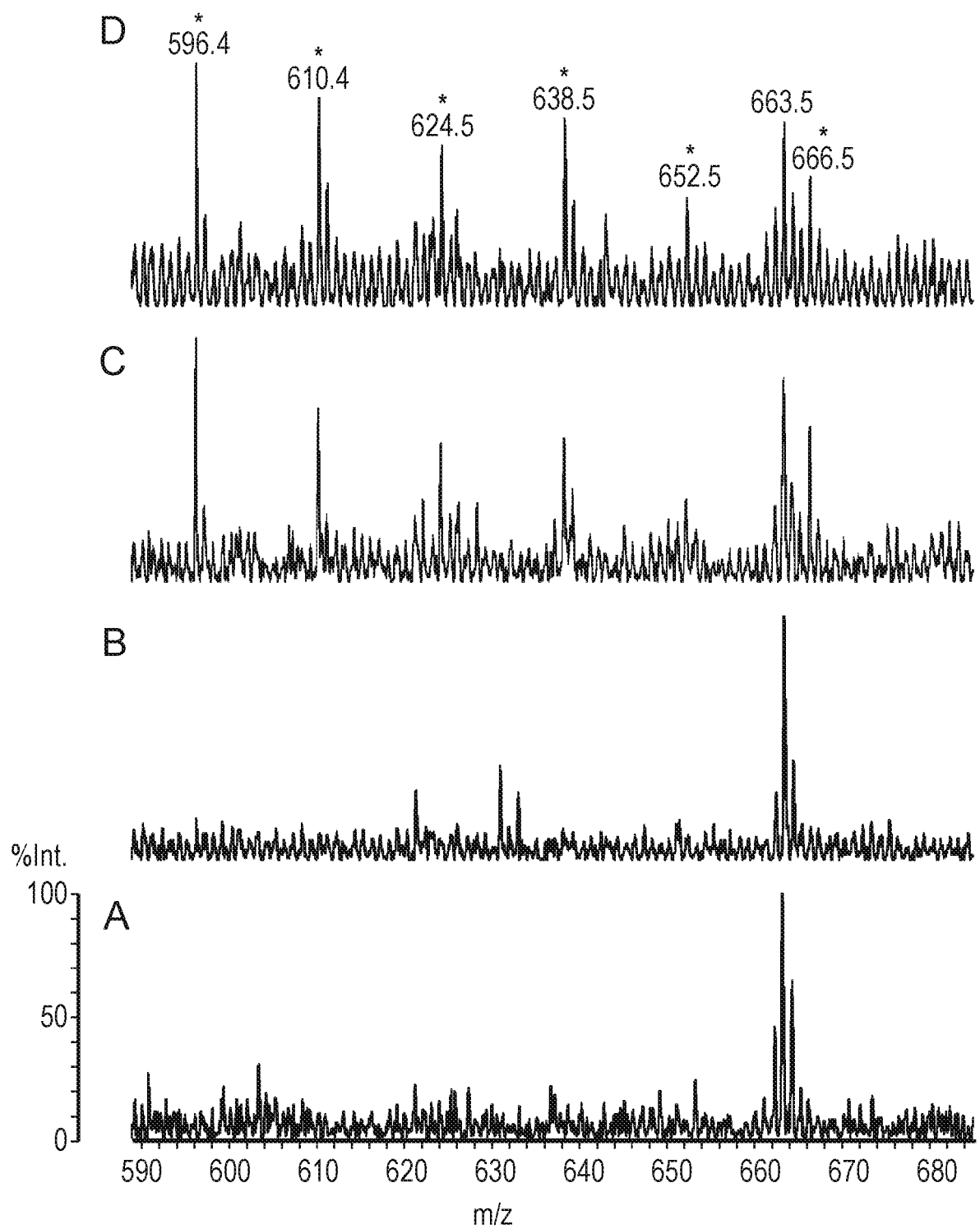
FIG. 13 shows the detection of endogenous OxPLs from mouse plasma using different NP-types. In A) the MALDI-MS spectra measured before and in B) after incubation with MAG-$NH_2$—NPs, in C) with $ZrO_2$—NPs, and in D) with MAG-PEA-NPs are shown. The peaks marked by asterisks represent OxPLs bound to the different NPs. In E) the identification of the different peaks based on m/z values and the retention times using LC-ESI-MS/MS and in F) a comparison between the relative signal intensities of the OxPLs detected by LC-MS and the approach described for the first time herein (termed "Nano-MALDI") are shown. The peak at m/z 663 represents a background signal related to a plasticizer (Irganox®168) leached out of the plastic materials used.[19]
Figure 13:
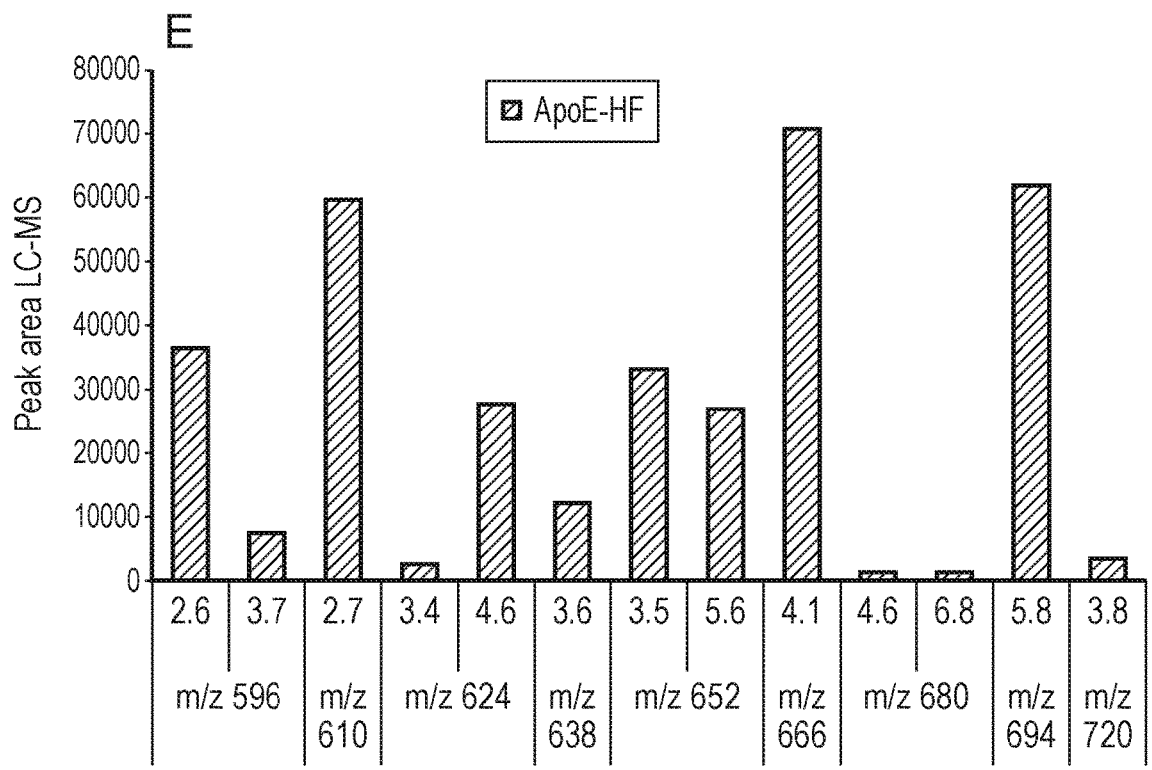
Figure 13:
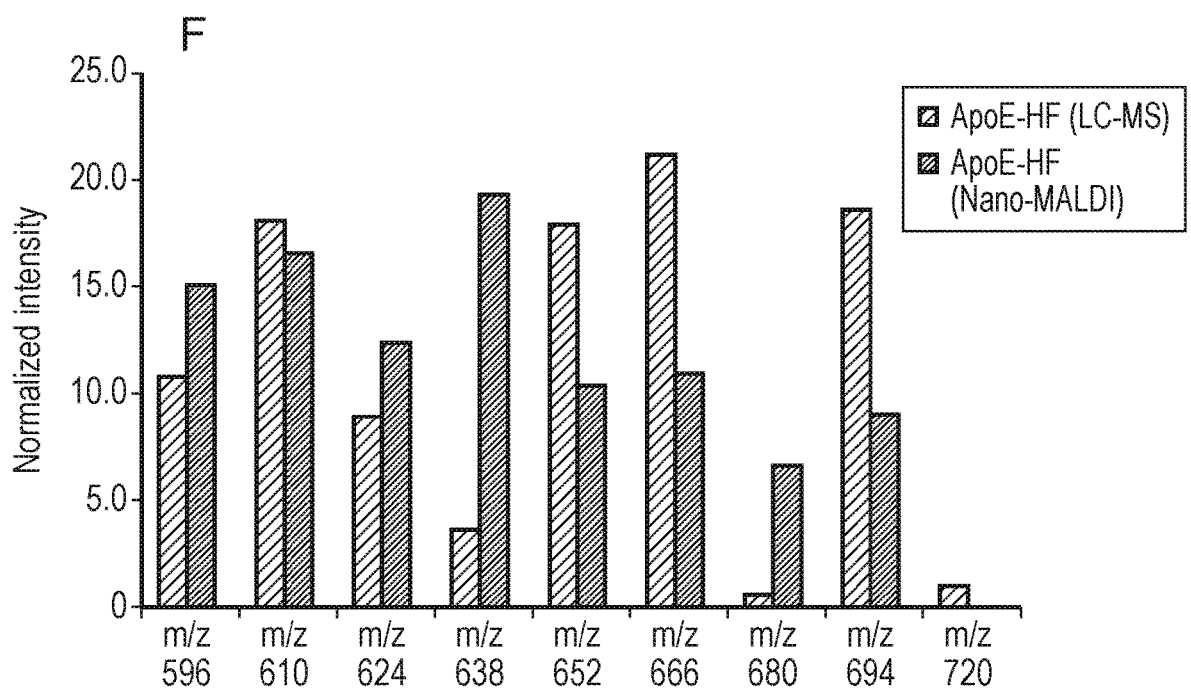
Figure 14:
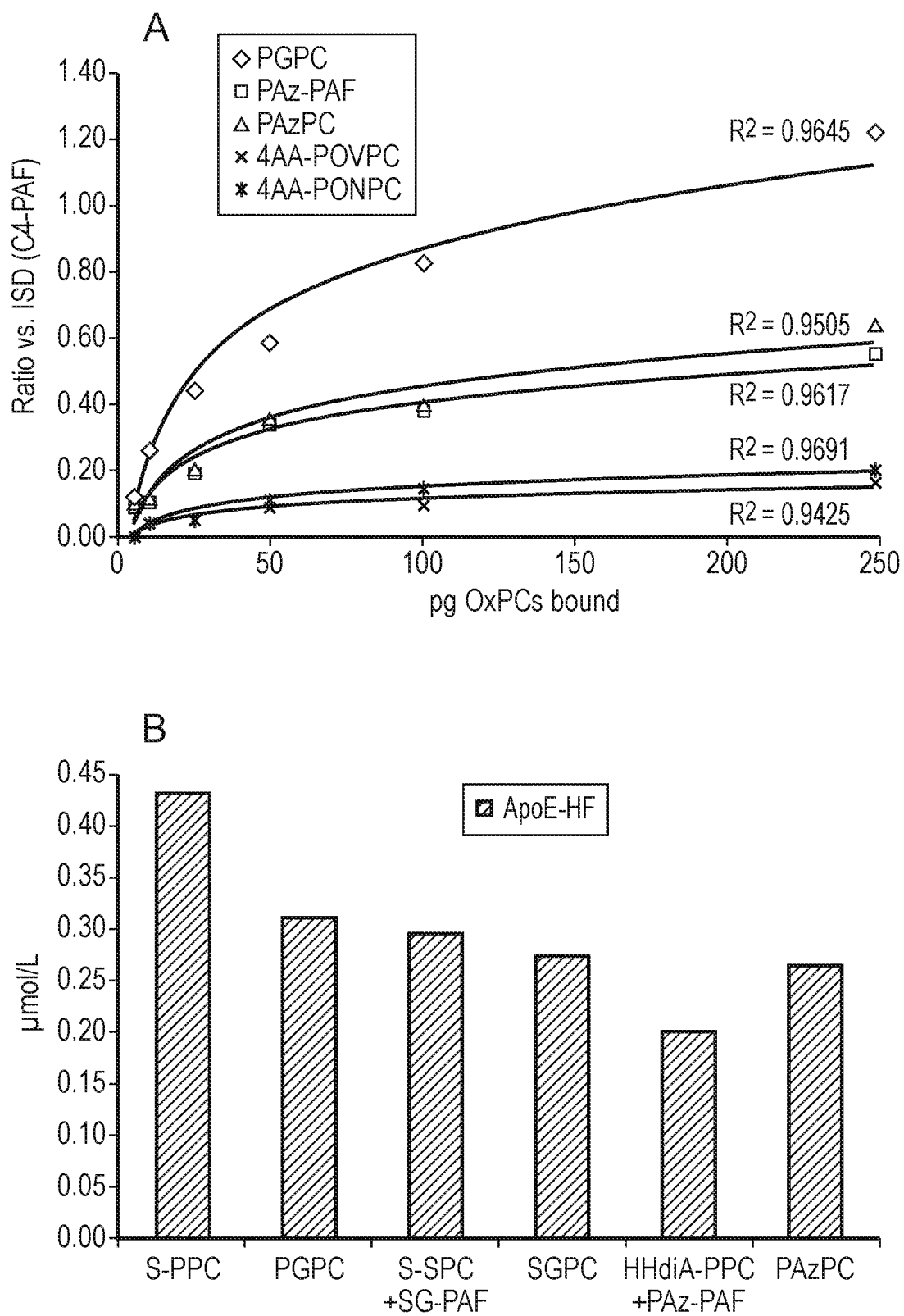
FIG. 14 shows the detection and quantification of OxPLs in mouse plasma and human oxidized lipoproteins. In A) the calibration curves of different OxPC standards detected by MALDI-MS after binding to MAG-PEA-NPs using 1-O-octadecyl-2-butyryl-sn-glycero-3-phosphocholine (C4-PAF) (m/z 580) as a structurally closely related internal standard (ISD) and in B) the calculated concentrations of OxPLs (i.e. OxPCs and OxPAFs) are shown. In panel C) the levels of LPCs and OxPLs displayed relative to the signal intensity of their precursor species and in D) the relative levels of the individual OxPL species detected by the Nano-MALDI approach are displayed. Plasma samples of ApoE−/− mice after a 3-months high-fat diet (ApoE-HF) were used.
Figure 14:
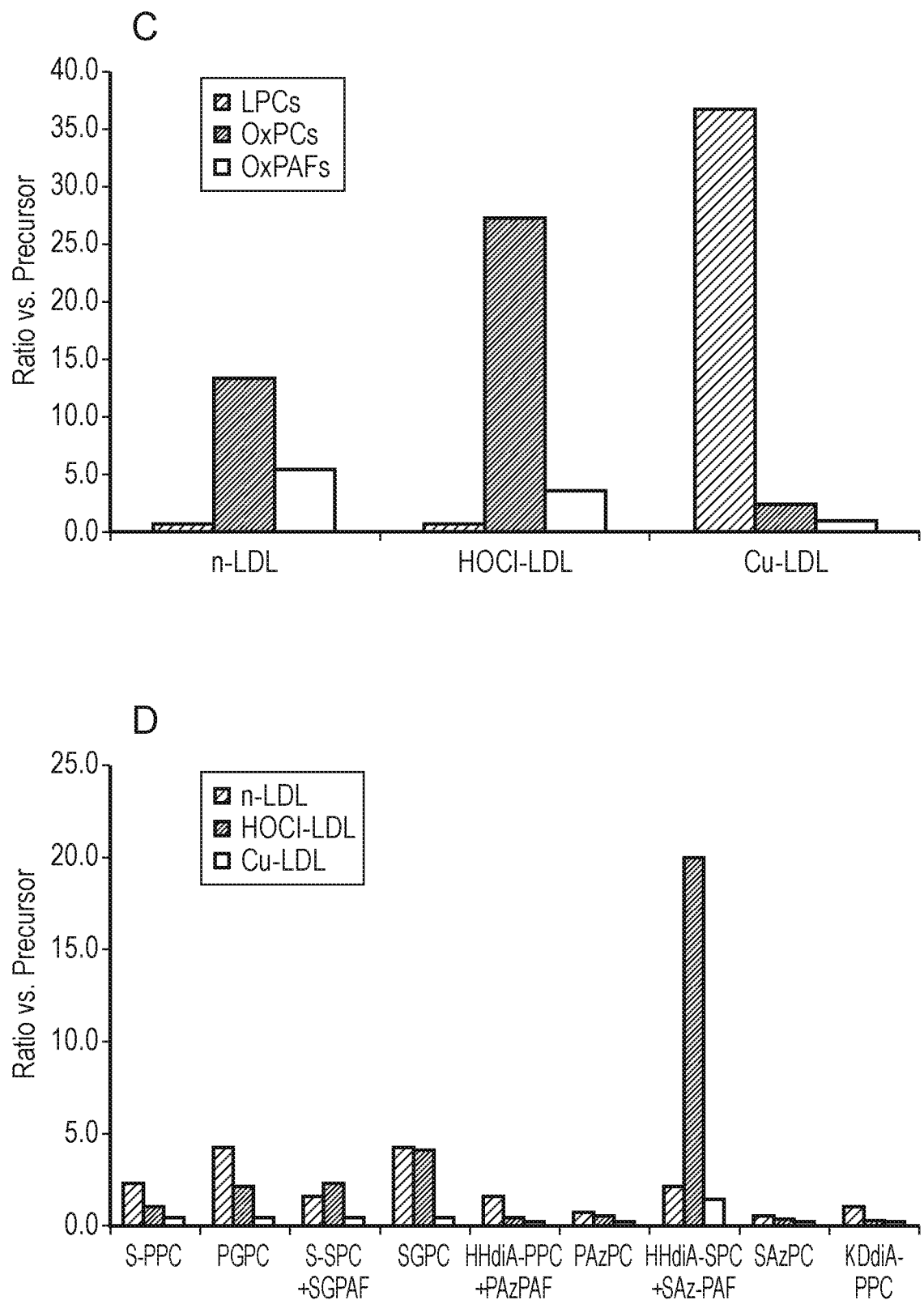

Using crude mouse plasma samples seven major peaks could be detected in the range of m/z 590-680 dependent on the used NP-type (see FIGS. 13 and 14), whereby the best enrichment of OxPLs was achieved using the MAG-PEA-NPs.

Figure 15:
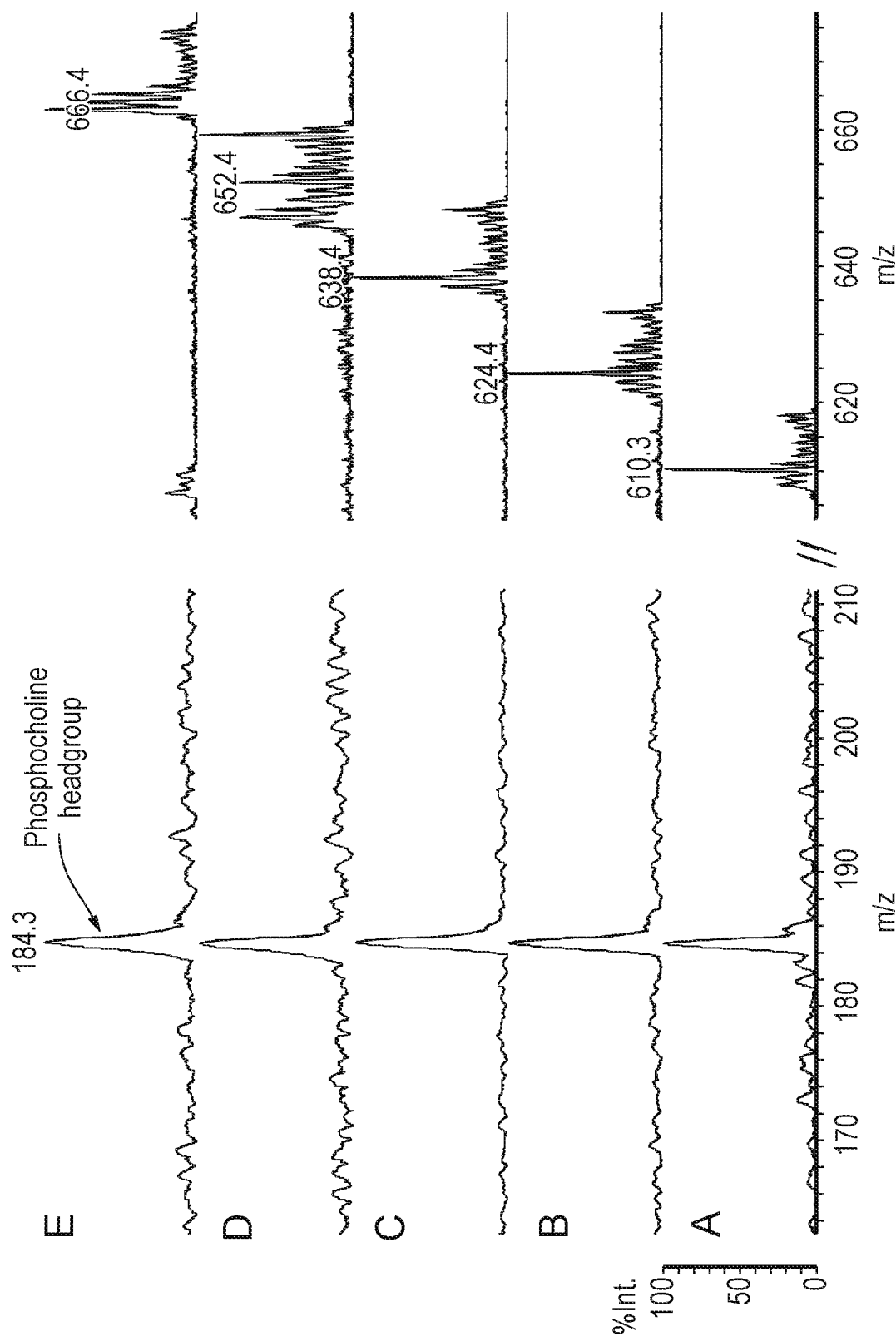
FIG. 15 shows MALDI-MS/MS analysis of endogenous OxPLs present in mouse plasma. The MALDI-post source decay (PSD) mass spectra of the peaks at A) m/z 610, B) m/z 624, C) m/z 638, D) m/z 652, and E) m/z 666 related to OxPLs detected on-probe by MALDI-MS after NP-binding from crude lipid extracts (see FIG. 13). Note the detection of the prominent diagnostic ion m/z 184 from the phosphocholine headgroup in all mass spectra (see left panel). A detection window of ±5 Da was used for selection of the precursor ions for MALDI-PSD analysis (see right panel).

The detection of the m/z 184 fragment ion within the MALDI-MS/MS spectra indicated that they correspond to OxPCs and/or OxPAFs (see FIG. 15). The identity of the peaks was confirmed by LC-ESI-SRM-MS/MS using authentic OxPC and OxPAF standards as reference compounds (FIG. 13E). These types of OxPLs are known to be present in atherosclerotic lesions and OxLDL[32], whereby OxPAFs were found to be biologically more active at same or even lower concentrations than the structurally corresponding OxPCs[33][34].

A comparison between the results obtained by Nano-MALDI and LC-ESI-MS shows distinct differences in the enrichment of the individual endogenous OxPL species from the mouse plasma samples. OxPLs containing very short-chain (C4-6) oxidized sn-2 residues (e.g. S—PPC) were more effectively captured by the MAG-PEA-NPs compared to OxPL enrichment using the C18 micro-columns (µHP-SPE) method.[21] (FIG. 13F).

Figure 16:
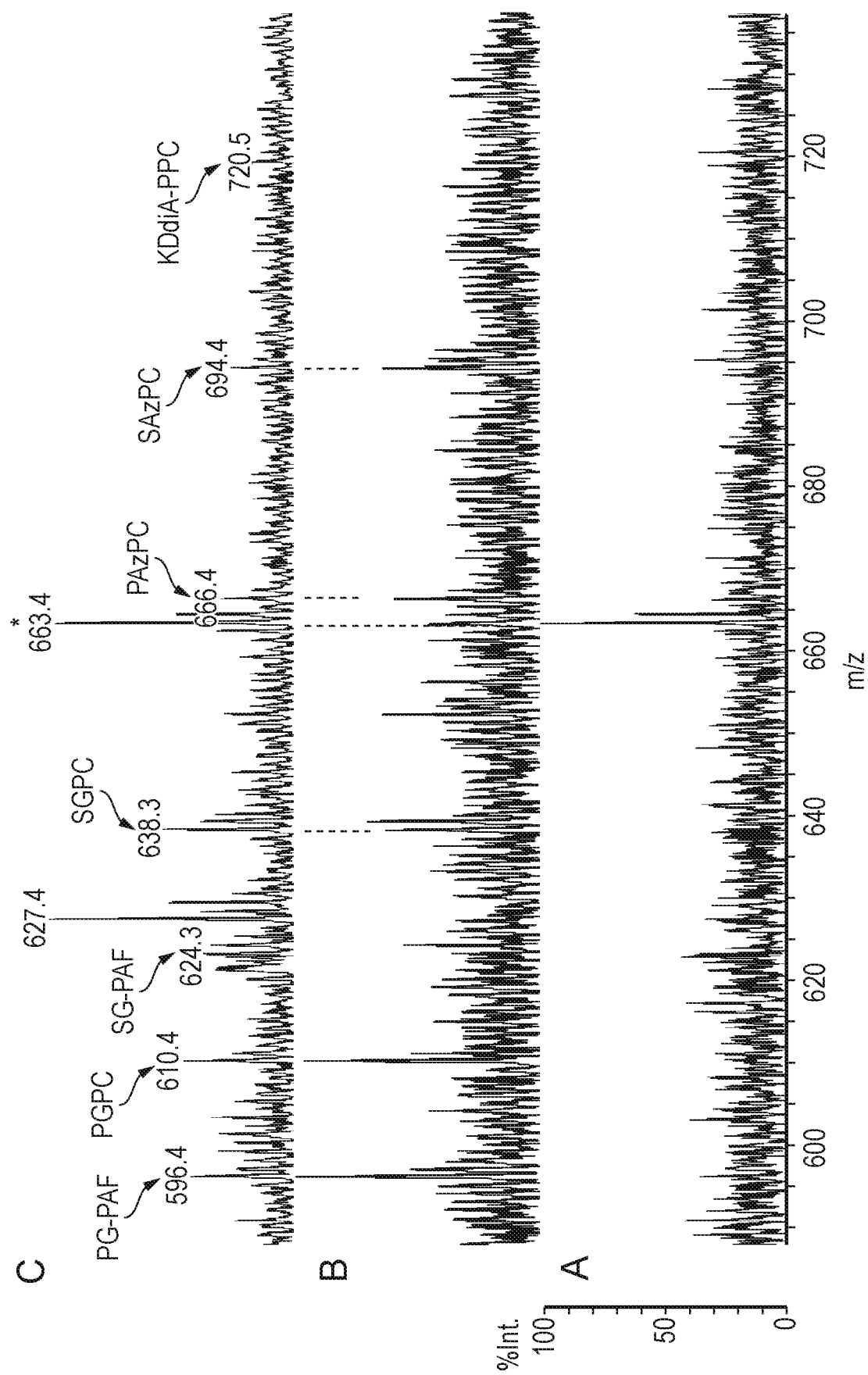
FIG. 16 shows MALDI spectra of endogenous OxPLs present in plasma of ApoE-deficient mice in vivo. The MALDI mass spectra of plasma lipid extracts of A) C57BL/6 wild type mice, B) ApoE−/− mice under normal diet (ApoE-ND), and C) ApoE−/− mice under high-fat diet (ApoE-HF) detected on-probe after binding to MAG-PEA-NPs are shown. Note the increased intensity of OxPC-related signals in the plasma samples of the ApoE-HF mice. The peak indicated by an asterisk (m/z 663) represents the $[M+H]^+$ ion of a plasticizer (Irganox®168) leached out of the plastic materials used.

By comparing plasma samples from C57BL/6 mice with those of ApoE-/- mice (i.e. an animal model for atherosclerosis), elevated levels of OxPLs in those fed a high-fat diet (ApoE-HF) were found (FIG. 16). Quantification of selected OxPLs in the ApoE-/- mouse plasma revealed a concentration range of ~0.2 up to 0.4 µM for the detected lipid species (FIGS. 14A and 14B).

This data is in agreement with previous studies demonstrating that these OxPL concentrations were sufficient to exhibit biological and pro-atherogenic activities (e.g. stimulation of monocytes or platelet activation)[35][36].

OxPL Profiling and Quantification from Human Samples

The above method was used for OxPL-profiling from in vitro oxidized human lipoproteins.

Figure 17:
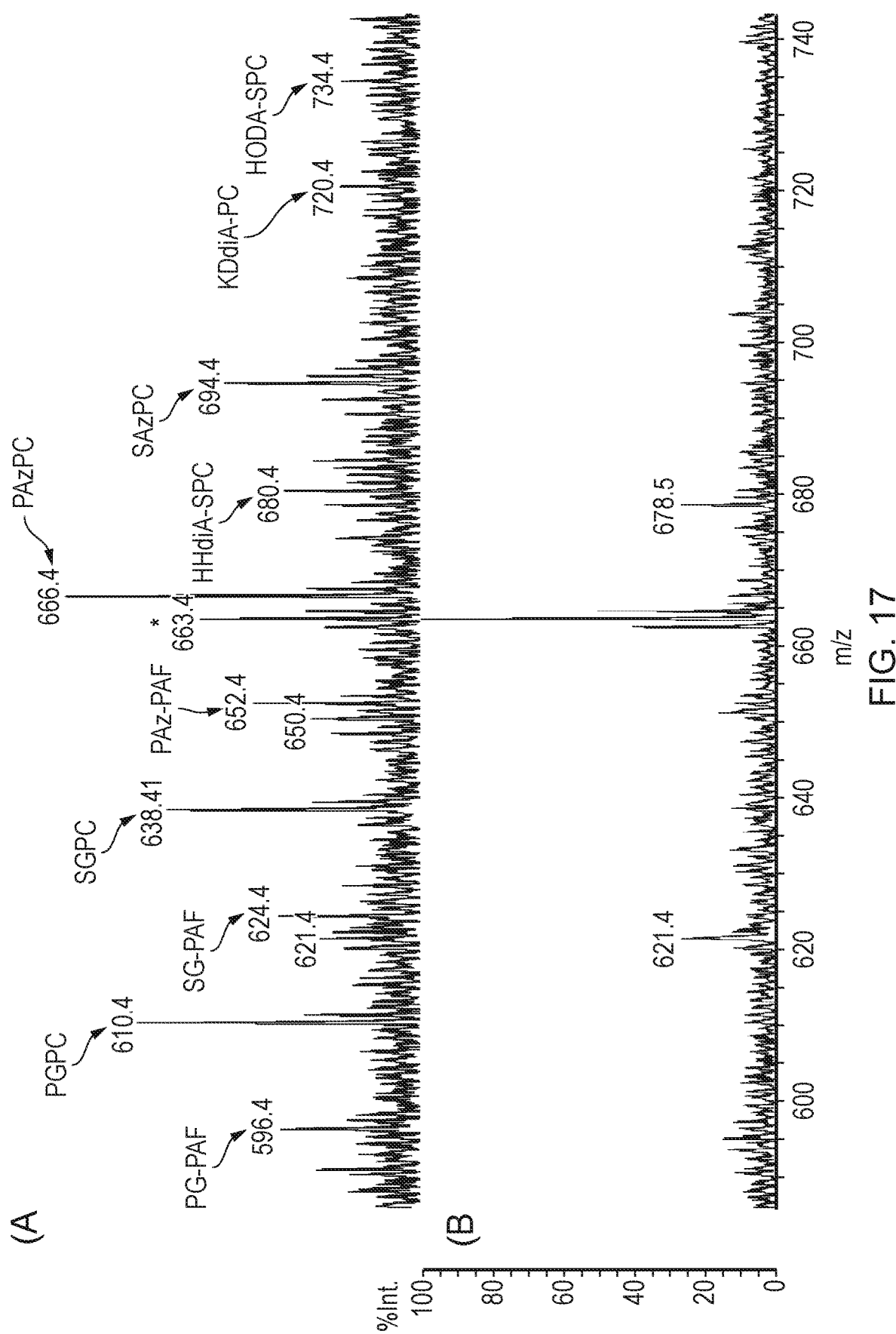
FIG. 17 shows MALDI spectra of endogenous OxPLs present in HOCl-modified LDL in vitro. The MALDI mass spectra of lipid extracts of A) HOCL-modified bovine serum albumin (HOCl-BSA) and B) HOCL-modified LDL (HOCl-LDL) detected on-probe after binding to MAG-PEA-NPs are shown. Note the absence of any OxPC-related signals in the mass spectrum of HOCl-BSA containing no oxidisable PLs. The peak indicated by an asterisk (m/z 663) represents the $[M+H]^+$ ion of a plasticizer (Irganox®168) leached out of the plastic materials used for sample preparation.
Figure 18:
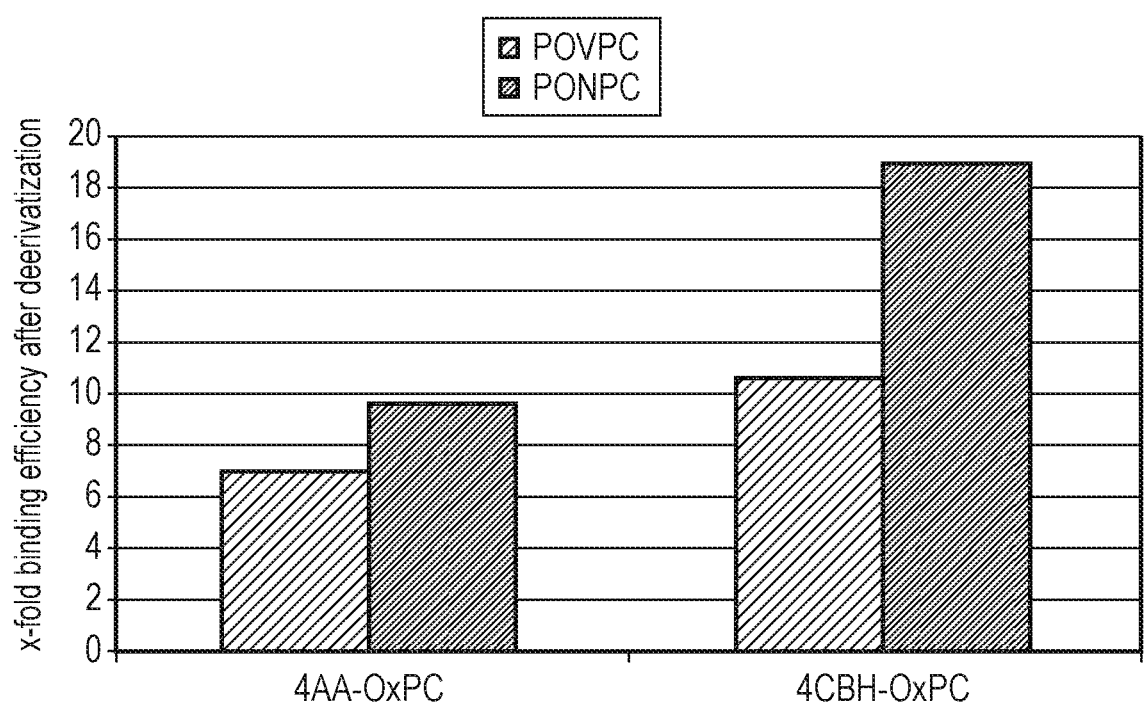
FIG. 18 shows the binding efficiency of ALDO-OxPCs after derivatisation with 4-AA and 4-CBH.

A number of peaks attributed to individual OxPC species (which were confirmed by LC-ESI-SRM-MS/MS) were detected in the MALDI mass spectra after NP-binding from the OxLDL samples (see FIG. 17).

The highest levels of OxPCs were found in HOCl-LDL and those of lyso-phosphatidylcholines (LPCs) (which are major degradation products of OxPCs) in Cu-LDL (FIG. 14C). A higher level of OxPLs were found in n-LDL compared to Cu-LDL suggesting more advanced breakdown of OxPLs to LPCs in the latter.

In a similar way to the mouse plasma testing (described above), HHdiA-SPC was found to be the major oxidation product within HOCl-LDL (FIG. 14D).

Consequently, these experiments demonstrate the suitability of this (Nano-MALDI) approach to deliver information about the composition and identity of oxidised lipid molecules (i.e. OxPLs) which are known to represent oxidative stress biomarkers of biological and clinical samples (e.g. human plasma and lipoproteins)

Thus this approach can be used in the development of novel (clinical) screening assays of these important oxidative stress biomarkers.

TABLE 1

| chemical name[a] | abbreviation | CN:DB number[b] | exact mass | ion species | supplier |
|---|---|---|---|---|---|
| 1-palmitoyl-2-hydroxy-sn-glycero-3-phosphocholine | LPC16:0 | sn-1 16:0[c] | 496.34 | $[M + H]^+$ | Avanti |
| 1-heptadecanoyl-2-hydroxy-sn-glycero-3-phosphocholine | LPC17:0 | sn-1 17:0[c] | 510.36 | $[M + H]^+$ | Avanti |
| 1-linolenoyl-2-hydroxy-sn-glycero-3-phosphocholine | LPC18:0 | sn-1 18:0[c] | 524.37 | $[M + H]^+$ | Avanti |
| 1-O-octadecyl-2-butyryl-sn-glycero-3-phosphocholine | C4-PAF | C18-4:0[e] (ISD) | 580.43 | $[M + H]^+$ | Avanti |
| 1,2-dimyristoyl-sn-glycero-3-phosphate | DMPA | 28:0 | 591.40 | $[M - H]^-$ | Avanti |
| 1-palmitoyl-2-(5-oxo-valeroyl)-sn-glycero-3-phosphocholine | POVPC | 21:0[f] (ALDO) | 594.38 | $[M + H]^+$ | Avanti |
| 1-palmitoyl-2-succinoyl-sn-glycero-3-phosphocholine | S-PPC | 20:0[f] (CARBO) | 596.36 | $[M + H]^+$ | n.a. |
| 1-palmitoyl-2-glutaroyl-sn-glycero-3-phosphocholine | PGPC | 21:0[f] (CARBO) | 610.37 | $[M + H]^+$ | Avanti |
| 1-stearoyl-2-(5-oxo-valeroyl)-sn-glycero-3-phosphocholine | SOVPC | 22:0 (ALDO) | 622.41 | $[M + H]^+$ | n.a. |
| 1-stearoyl-2-succinoyl-sn-glycero-3-phosphocholine | S-SPC | 22:0 (CARBO) | 624.39 | $[M + H]^+$ | n.a. |
| 1-O-octadecyl-2-glutaroyl-sn-glycero-3-phosphocholine | SG-PAF | C18-5:0[e] (CARBO) | 624.42 | $[M + H]^+$ | n.a. |

TABLE 1-continued

| chemical name[a] | abbreviation | CN:DB number[b] | exact mass | ion species | supplier |
|---|---|---|---|---|---|
| 1,2-dimyristoyl-sn-glycero-3-phosphoethanolamine | DMPE | 28:0 | 634.45 | [M − H]− | Avanti |
| 1-stearoyl-2-glutaroyl-sn-glycero-3-phosphocholine | SGPC | 22:0 (CARBO) | 638.40 | [M + H]+ | n.a. |
| 1-palmitoyl-2-(9-oxo-nonanoyl)-sn-glycero-3-phosphocholine | PONPC | 25:0[f] (ALDO) | 650.44 | [M + H]+ | Avanti |
| 1-palmitoyl-2-(5-hydroxy-8-oxoocta-6-enoyl)-sn-glycero-3- | HOOA-PPC | 24:1[f] (ALDO) | 650.40 | [M + H]+ | n.a. |
| 1-palmitoyl-2-(4-hydroxy-7-carboxy-hex-5-enoyl)-sn-glycero-3-phosphocholine | HHdiA-PPC | 23:1[f] (CARBO) | 652.38 | [M + H]+ | n.a. |
| 1-O-hexadecyl-2-azelaoyl-sn-glycero-3-phosphocholine | PAz-PAF | C16-9:0[e] (CARBO) | 652.46 | [M + H]+ | Sigma |
| 1-palmitoyl-2-azelaoyl-sn-glycero-3-phosphocholine | PAzPC | 25:0[f] (CARBO) | 666.44 | [M + H]+ | Avanti |
| 1-palmitoyl-2-(7-carboxy-5-hydroxyhept-6-enoyl)-sn-glycero-3-phosphocholine | HOdiA-PPC | 24:1[f] (CARBO) | 666.40 | [M + H]+ | n.a. |
| 1,2-dimyristoyl-sn-glycero-3-phosphoserine | DMPS | 28:0 | 678.44 | [M − H]− | Avanti |
| 1,2-dimyristoyl-sn-glycero-3-phosphocholine | DMPC | 28:0 | 678.51 | [M + H]+ | Avanti |
| 1-stearoyl-2-(4-hydroxy-7-carboxyhex-5-enoyl)-sn-glycero-3-phosphocholine | HHdiA-SPC | 25:1[f] (CARBO) | 680.41 | [M + H]+ | n.a. |
| 1-O-octadecyl-2-azelaoyl-sn-glycero-3-phosphocholine | SAz-PAF | 27:0[e] (CARBO) | 680.45 | [M + H]+ | n.a. |
| 1-stearoyl-2-azelaoyl-sn-glycero-3-phosphocholine | SAzPC | 27:0 (CARBO) | 694.47 | [M + H]+ | n.a. |
| N-palmitoyl-D-erythro-sphingosylphosphorylcholine | SM16:0 | C18-16:0[d] | 703.58 | [M + H]+ | Avanti |
| 1-palmitoyl-2-(9,12-dioxododec-10-enoyl)-sn-glycero-3-phosphocholine | KODA-PPC | 28:1[f] (ALDO) | 704.45 | [M + H]+ | n.a. |
| 1-palmitoyl-2-(11-carboxy-9-oxoundec-6-enoyl)-sn-glycero-3-phosphocholine | KDdiA-PPC | 28:1[f] (CARBO) | 720.45 | [M + H]+ | Cayman |
| 1-palmitoyl-2-(9-hydroxy-11-carboxyundec-6-enoyl)-sn-glycero-3-phosphocholine | HDdiA-PPC | 28:1[f] (CARBO) | 722.46 | [M + H]+ | n.a. |
| 1-stearoyl-2-(9-hydroxy-12-oxododec-10-enoyl)-sn-glycero-3-phosphocholine | HODA-SPC | 30:1[f] (ALDO) | 734.50 | [M + H]+ | n.a. |
| 1-palmitoyl-2-linoleoyl-sn-glycero-3-phosphocholine | PLPC | 34:2 | 758.57 | [M + H]+ | Avanti |
| 1-palmitoyl-2-arachidonoyl-sn-glycero-3-phosphocholine | PAPC | 36:4 | 782.57 | [M + H]+ | Avanti |
| 1-stearoyl-2-linoleoyl-sn-glycero-3-phosphocholine | SLPC | 36:2 | 786.60 | [M + H]+ | Avanti |
| 1-palmitoyl-2-(9-hydroxy-linoleoyl)-sn-glycero-3-phosphocholine | PLPC-OH | 34:2[g] | 774.57 | [M + H]+ | n.a. |
| 1-palmitoyl-2-(9-hydroperoxy-linoleoyl)-sn-glycero-3-phosphocholine | PLPC-OOH | 34:2[g] | 790.56 | [M + H]+ | n.a. |
| 1-heptadecanoyl-2-(9Z-tetradecenoyl)-sn-glycero-3-phospho-(1'-myo-inositol) | HMPI | 31:1 | 793.49 | [M − H]− | Avanti |
| 1-palmitoyl-2-(9-hydroxy-14-hydroperoxy-linoleoyl)-sn-glycero-3-phosphocholine | PLPC-(OH)OOH | 34:2[g] | 806.56 | [M + H]+ | n.a. |
| 1-palmitoyl-2-(5,6-epoxycyclopentenone)-sn-glycero-3-phosphocholine | PECPC | 36:3[h] | 810.53 | [M + H]+ | n.a. |
| 1-palmitoyl-2-(5,6-epoxyisoprostane)-sn-glycero-3-phosphocholine | PEIPC | 36:2[h] | 828.54 | [M + H]+ | n.a. |
| 1-stearoyl-2-docosahexaenoyl-sn-glycero-3-phosphocholine | SDPC | 40:6 | 834.60 | [M + H]+ | Avanti |
| 1-palmitoyl-2-(11,15-dihydroperoxy-arachidonoyl)-sn-glycero-3-phosphocholine | PAPC-(OOH)$_2$ | 36:4[g] | 846.55 | [M + H]+ | n.a. |

TABLE 1-continued

| chemical name[a] | abbreviation | CN:DB number[b] | exact mass | ion species | supplier |
|---|---|---|---|---|---|
| 1',3'-bis[1,2-dimyristoyl-sn-glycero-3-phospho]-sn-glycerol | TMCL | 56:0 | 1239.84 | $[M - H]^-$ | Avanti |

[a]Nomenclature according to the LIPID MAPS classification standard
[b]Total number of carbon atoms and double bonds of the sn-1 and sn-2 fatty acid residues esterified to the glycerol backbone of the PL molecules.
[c]LPC contain only one fatty acid together with a free hydroxyl group either in sn-1 or sn-2 position. In human plasma saturated fatty acids (e.g. 16:0 or 18:0) are preferentially linked to the sn-1 position[37]
[d]SM contains one fatty acid linked via amide bond to a sphingosine backbone (long-chain base consisting of C18 or C20 carbon atoms)[38]
[e]PAFs contain one sn-2 fatty acid residue (usually C2-C4 carbon atoms) and one sn-1 ether-linked carbon chain (with C16 or C18 carbon atoms)[39]
[f]For the chemical structures see[40]
[g]For the isobaric structures[41]
[h]For the chemical structures[42]
ALDO - OxPC containing sn-2 short-chain ω-terminal aldehydic fatty acid residue
CARBO - OxPC containing sn-2 short-chain ω-terminal carboxylic fatty acid residue
ISD, internal standard (synthetic compound)

REFERENCES

A number of publications are cited above in order to more fully describe and disclose the invention and the state of the art to which the invention pertains. Full citations for these references are provided below. The entirety of each of these references is incorporated herein.
[1] P. Libby Nature 2002, 420:868-874
[2] Podrez et al. Nat. Med. 2007, 13:1086-1095
[3] J. A. Berliner and A. D. Watson N. Engl. J. Med. 2005, 353:9-11
[4] F. H. Greig et al. Free Rad. Biol. Med. 2012, 52, 266-280
[5] N. Leitinger Mol. Aspects Med. 2003, 24, 239-250
[6] L. J. Sparvero et al. J. Neurochem. 2010, 115, 1322-1336
[7] Stübiger et al. Anal. Chem. 2010, 82, 5502-5510
[8] M. Schlame et al. J. Lipid Res. 1996, 37, 2608-2615
[9] Frey et al. J. Lipid Res. 2000, 41, 1145-1153
[10] A. D. Watson et al. J. Biol. Chem. 1999, 274, 24787-24798
[11] K. A. Harrison et al. J. Mass Spectrom 2000, 35, 224-236
[12] X. Chen et al. J. Lipid Res. 2008, 49, 832-846
[13] I. Milic et al. Anal. Chem. 2013, 85, 156-162
[14] K. Teuber et al. Anal. Lett. 2012, 45, 968-976
[15] Stübiger et al. Atherosclerosis 2012, 224, 177-186
[16] Reis A. et al., Biochim. Biophys. Acta 2012, 1818, 2374-2387
[17] Moumtzi A. et al., 2007, J. Lipid Res. 48:565-582
[18] N. Auge et al. Arterioscler. Thromb. Vasc. Biol. 1990, 22, 1990-1995
[19] J. Wu et al. Chem. Phys. Lipids 2011, 164, 1-8.
[20] Z. Zhao and Y. Xu J. Lipid Res. 2010; 51:652-659
[21] Podrez et al. Nat. Med. 2007, 13:1086-1095
[22] G. Sun et al. Anal. Chem. 2008, 80, 7576-7585
[23] R. L. Martin and F. L. Brancia 2003, Rapid Commun. Mass Spectrom. 17, 1358-1365
[24] Yan. Li et al. J. Proteome Res. 2008, 7, 2526-2538.
[25] Ana Gonzálvez et al. Anal. Bioanal. Chem. 2010, 396, 2965-2975
[26] Grady R. Blacken et al. Anal. Chem. 2007, 79, 5449-5456
[27] Robert N. Grass et al. Angew. Chem. Int. Ed. 2007, 46, 4909-4912
[28] Yan. Li et al. J. Proteome Res. 2008, 7, 2526-2538
[29] Podrez et al. Nat. Med. 2007, 13:1086-1095.
[30] B. Frey et al. J. Lipid Res. 2000; 41:1145-1153
[31] Stübiger et al. Atherosclerosis 2012, 224, 177-186
[32] K. Gopal et al. Trends Cardiovasc. Med. 2001, 11, 139-142
[33] H. Kern et al. Biochim. Biophys. Acta 1998, 1394, 33-42
[34] X. Chen et al. J. Lipid Res. 2008, 49, 832-846
[36] H. Kern et al. Biochim. Biophys. Acta 1998, 1394, 33-42
[36] E. A. Podrez et al. Nat. Med. 2007, 13:1086-1095

[37] P V. Subbaiah et al. Biochim. Biophys. Acta 1992; 1128:83-92
[38] B. Ramstedt et al. Eur. J. Biochem. 1999; 266:997-1002
[39] S M. Prescott Annu. Rev. Biochem. 2000; 69:419-445
[40] S L. Hazen J. Biol. Chem. 2008, 283, 15527-15531.
[41] A. Reis J. Mass Spectrom. 2004; 39: 1513-1522
[42] G. Subbanagounder J. Biol. Chem. 2002, 277, 7271-7281.

The invention claimed is:
1. A method of extracting oxidised lipids from a lipid solution, the method comprising
 (a) a derivatisation step, comprising:
  (i) a reductive amination of aldehydic oxidised lipids present in the lipid solution, comprising
   contacting the lipid solution with a derivatisation agent selected from 2-aminoanthranilic acid (2AA), 4-aminoanthranilic acid (4AA), 3-(4-aminophenyl)-propionic acid (4APA) and 6-aminocaproic acid (6ACA), such that the aldehydic oxidised lipids present in the lipid solution are derivatised to include a carboxy group; or
  (ii) a hydrazone formation with aldehydic oxidised lipids and/or α,β-unsaturated oxidised lipids present in the lipid solution, comprising
   contacting the lipid solution with a derivatisation agent that is a compound according to formula (I):

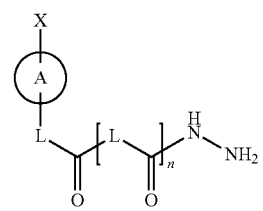

(I)

or a salt, solvate or hydrate thereof
wherein:
X represents a carboxy group
each L independently represents a single bond or linker group
n is an integer from 0 to 4, and
A represents an optionally substituted heteroaryl or aryl group,
such that the aldehydic oxidised lipids and/or α,β-unsaturated oxidised lipids present in the lipid solution are derivatised to include a carboxy group; and
 (b) an oxidised lipid capture step, in which nanoparticles are contacted with the lipid solution, wherein the nanoparticles capture carboxy group containing oxidised lipids.
2. A method according to claim 1, wherein the nanoparticles comprise a metal oxide.

3. A method according to claim 1, wherein the nanoparticles comprise a magnetic core and a surface, and wherein the nanoparticles are functionalised such that the surface is electrophilic.

4. A method according to claim 3, wherein the magnetic core comprises iron oxide.

5. A method according to claim 3, wherein the magnetic core is surface functionalised such that the surface is hydrophilic; and/or the surface binds carboxy group containing oxidised lipids by an anion-exchange mechanism; and/or the surface comprises a polymer; and/or the surface comprises or consists of amines or polyetheramines.

6. A method according to claim 1, wherein for the reductive amination of (i), the aldehydic oxidised lipids present in the lipid solution are derivatised to include an aromatic group.

7. A method according to claim 1, wherein the derivatisation step comprises the hydrazone formation of (ii).

8. The method according to claim 7, wherein the derivatisation agent is

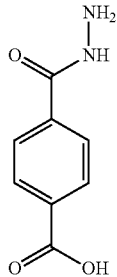

or a salt, solvate or hydrate thereof.

9. A method according to claim 1, further comprising an initial step of lipid extraction, comprising extraction of the lipid solution from a biological sample.

10. A method according to claim 1, wherein in step (b) the nanoparticles are added to the lipid solution, and further comprising after step (b), (ci) an extraction step, comprising extraction of the nanoparticles from the lipid solution.

11. A method according to claim 10, wherein the nanoparticles are extracted from the lipid solution by centrifugation or by using a magnet.

12. A method according to claim 10, wherein the nanoparticles are fixed to a surface, and further comprising after step (ci), (cii) a washing step, comprising washing the surface to remove excess lipid solution.

13. A method according to claim 12, further comprising after step (cii), (d) a data gathering step, in which data representative of the aldehydic oxidised lipids of (i) or the aldehydic oxidised lipids and/or α,β-unsaturated oxidised lipids of (ii) is obtained.

14. A method according to claim 13, further comprising (e) a data analysis step, in which the aldehydic oxidised lipids of (i) or the aldehydic oxidised lipids and/or α,β-unsaturated oxidised lipids of (ii) are detected, quantified and/or identified based on the data obtained.

* * * * *